US010006840B2

(12) United States Patent
Kauling et al.

(10) Patent No.: US 10,006,840 B2
(45) Date of Patent: Jun. 26, 2018

(54) TECHNOLOGY FOR PURIFYING NK CELLS AND OTHER CELL TYPES BY CONCURRENT GRAVITY SEDIMENTATION AND MAGNETIC SEPARATION

(71) Applicant: Miltenyi Biotech GmbH, Bergisch Gladbach (DE)

(72) Inventors: Burgund Kauling, Bergisch Gladbach (DE); Volker Huppert, Kürten (DE)

(73) Assignee: Miltenyi Biotec GmbH, Bergisch Gladach (DE)

( * ) Notice: Subject to any disclaimer, the term of this patent is extended or adjusted under 35 U.S.C. 154(b) by 0 days. days.

(21) Appl. No.: 14/358,922

(22) PCT Filed: Nov. 20, 2012

(86) PCT No.: PCT/EP2012/073083
§ 371 (c)(1),
(2) Date: May 16, 2014

(87) PCT Pub. No.: WO2013/076070
PCT Pub. Date: May 30, 2013

(65) Prior Publication Data
US 2014/0302483 A1 Oct. 9, 2014

(30) Foreign Application Priority Data

Nov. 25, 2011 (EP) ..................................... 11190850

(51) Int. Cl.
A01N 1/02 (2006.01)
G01N 33/00 (2006.01)
C12N 5/071 (2010.01)
G01N 1/34 (2006.01)
B01D 21/00 (2006.01)
C12Q 1/02 (2006.01)
C12N 5/00 (2006.01)
B03C 1/01 (2006.01)
B03C 1/28 (2006.01)
B01D 21/26 (2006.01)

(52) U.S. Cl.
CPC .............. *G01N 1/34* (2013.01); *B01D 21/00* (2013.01); *B03C 1/01* (2013.01); *B03C 1/288* (2013.01); *C12N 5/0087* (2013.01); *C12Q 1/02* (2013.01); *B01D 21/0009* (2013.01); *B01D 21/262* (2013.01); *B03C 2201/26* (2013.01)

(58) Field of Classification Search
CPC ........ B03C 1/01; B01D 21/00; G01N 33/539; G01N 1/34; G01N 33/00; G01N 33/53; C12N 5/06; C12N 5/08; C12N 5/0087; C12N 5/071; A01N 1/02; C12Q 1/02
USPC ............ 435/2, 7.24, 7.25, 372, 372.2, 372.3
See application file for complete search history.

(56) References Cited

U.S. PATENT DOCUMENTS

| 3,586,413 | A | 6/1971 | Adams |
| 3,700,555 | A | 10/1972 | Widmark et al. |
| 3,955,755 | A | 5/1976 | Breillatt et al. |
| 4,111,199 | A * | 9/1978 | Djerassi ............... A61B 5/1405 436/63 |
| 4,632,908 | A | 12/1986 | Schultz |
| 5,260,598 | A | 11/1993 | Brass et al. |
| 5,316,667 | A | 5/1994 | Brown et al. |
| 5,691,208 | A | 11/1997 | Miltenyi |
| 5,904,840 | A | 5/1999 | DiBella |
| 6,080,581 | A | 6/2000 | Andeson |
| 6,709,377 | B1 | 3/2004 | Rochat |
| 6,933,148 | B2 * | 8/2005 | Collins et al. ................ 435/372 |
| 2002/0144939 | A1 | 10/2002 | Dolecek |
| 2002/0173034 | A1 | 11/2002 | Barbera-Guillem |
| 2003/0134416 | A1 * | 7/2003 | Yamanishi .............. A61M 1/36 435/372 |

(Continued)

FOREIGN PATENT DOCUMENTS

| EP | 0016552 A | 10/1980 |
| EP | 0654669 A | 5/1995 |

(Continued)

OTHER PUBLICATIONS

BD CD Marker Handbook (2010), downloaded from http://www.bdbiosciences.com/documents/cd_marker_handbook.pdf on Dec. 17, 2015.*
Santamaria et al. Inhibition of Eotaxin-Mediated Human Eosinophil Activation and Migration by the Selective Cyclic Nucleotide Phosphodiesterase Type 4 Inhibitor Rolipram; British Journal of Pharmacology, vol. 121 (1997) pp. 1150-1154.*
International Search Report and Written Opinion for European Patent Application No. 11190850.5, dated Apr. 27, 2012.
International Search Report and Written Opinion for European Patent Application No. 11190850.5, dated Oct. 12, 2013.
International Search Report and Written Opinion for European Patent Application No. 11190850.5, dated Oct. 4, 2014.
International Search Report and Written Opinion for PCT Application No. PCT/IB2008/003845, dated Jun. 8, 2010.
International Search Report and Written Opinion for PCT Application No. PCT/EP2012/073083, dated May 27, 2014.

(Continued)

*Primary Examiner* — Scott Long
*Assistant Examiner* — Paul Martin
(74) *Attorney, Agent, or Firm* — Kilpatrick Townsend & Stockton LLP

(57) ABSTRACT

The present invention provides methods and compositions for separating cells from a sample containing erythrocytes. The method is for recovering desired cells from a sample containing the desired cells, erythrocytes and undesired cells comprising: a) contacting the sample with a composition, said composition comprising: i) an erythrocytes aggregation reagent ii) at least one antigen recognizing moiety coupled to a magnetic particle, wherein said particle with said at least one antigen recognizing moiety specifically binds to at least one antigen specific for one or more undesired cellular components; b) applying simultaneously i) gravity sedimentation for sedimentation of erythrocytes and ii) a magnetic field gradient to said sample for immobilizing said magnetic particle generating a pellet and a supernatant phase, and c) recovering the desired cells from the supernatant phase. Compositions for the use within the present method are also disclosed.

28 Claims, 16 Drawing Sheets

(56) References Cited

U.S. PATENT DOCUMENTS

| | | | |
|---|---|---|---|
| 2007/0207128 A1* | 9/2007 | Lazarus | C07K 16/00 424/93.7 |
| 2008/0248011 A1* | 10/2008 | Nakagawa | C07K 16/2803 424/93.71 |
| 2010/0311559 A1 | 12/2010 | Miltenyi et al. | |
| 2013/0266930 A1* | 10/2013 | Dinges | G01N 33/5375 435/5 |

FOREIGN PATENT DOCUMENTS

| | | |
|---|---|---|
| JP | 2005052071 | 3/2005 |
| WO | 90/04019 A | 4/1990 |
| WO | 2002/083262 A1 | 10/2002 |
| WO | 2002083262 | 10/2002 |
| WO | 2009/072006 A2 | 6/2009 |
| WO | 2010087283 | 8/2010 |

OTHER PUBLICATIONS

Hildebrandt et al., "Immunomagnetic Selection of CD34+ Cells: Factors Influencing Component Purity and Yield," Transfusion 40(5): 507-512 (2000).

Preti et al., "The Combined Use of Soybean Agglutinin and Immunomagnetic Beads for T Lymphocyte Subset Depletion of Bone Marrow Allografts: A Laboratory Analysis," Journal of Hematotherapy 3(2): 111-120 (1994).

\* cited by examiner

FIG 8

| specificity | starting frequency | final frequency | removal efficiency |
|---|---|---|---|
| 2 antibodies, CD61, CD15, 200nm beads | | | |
| CD61 | n.d. | n.d. | n.d. |
| CD15 | 33% | 0.01% | 99.9% |
| 3 antibodies, CD3, CD19, CD61, 50nm beads | | | |
| CD3 | 28% | 1.4% | 99% |
| CD19 | 8% | 2% | 92% |
| CD61 | n.d. | n.d. | n.d. |
| 3 antibodies, CD3, CD19, CD61, 290nm beads | | | |
| CD3 | 28% | 0.05% | 99.9% |
| CD19 | 8.2% | 0.01% | 99.9% |
| CD61 | n.d. | n.d. | n.d. |
| 4 antibodies, CD3, CD15, CD19, CD61, 50nm beads | | | |
| CD14 | 10.6% | 0.3% | 98% |
| CD15 | 48.8% | 4.7% | 53% |
| CD19 | 8.1% | 0.1% | 99% |
| CD61 | n.d. | n.d. | n.d. |
| 6 antibodies, CD3, CD4, CD14, CD15, CD19, CD61, 50 nm beads | | | |
| CD3 | 70.3% | 5.5% | 99% |
| CD4dim | 16% | 13.2% | 94% |
| CD4bright | 44.8% | 0.01% | 99.9% |
| CD14 | 10.6% | 2.6% | 98% |
| CD15 | 48.8% | 49.3% | 92% |
| CD19 | 8.1% | 0.3% | 99.9% |
| CD61 | n.d. | n.d. | n.d. |

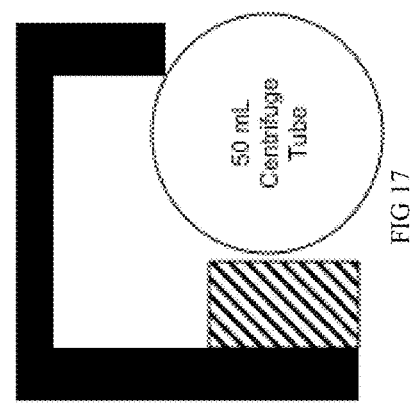
FIG 17
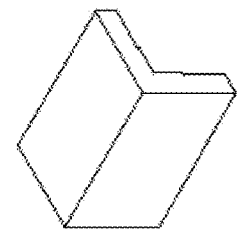
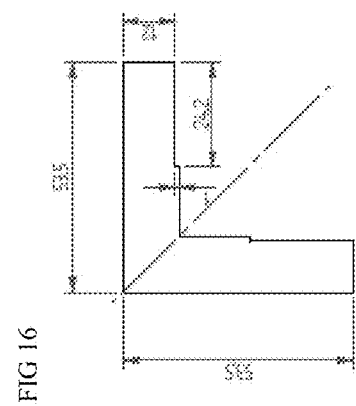
FIG 16
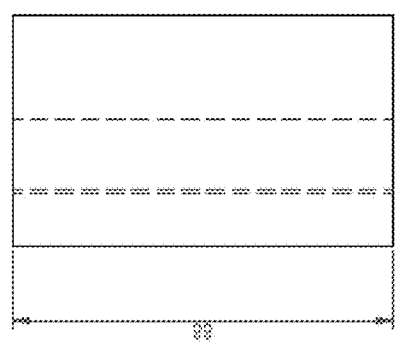

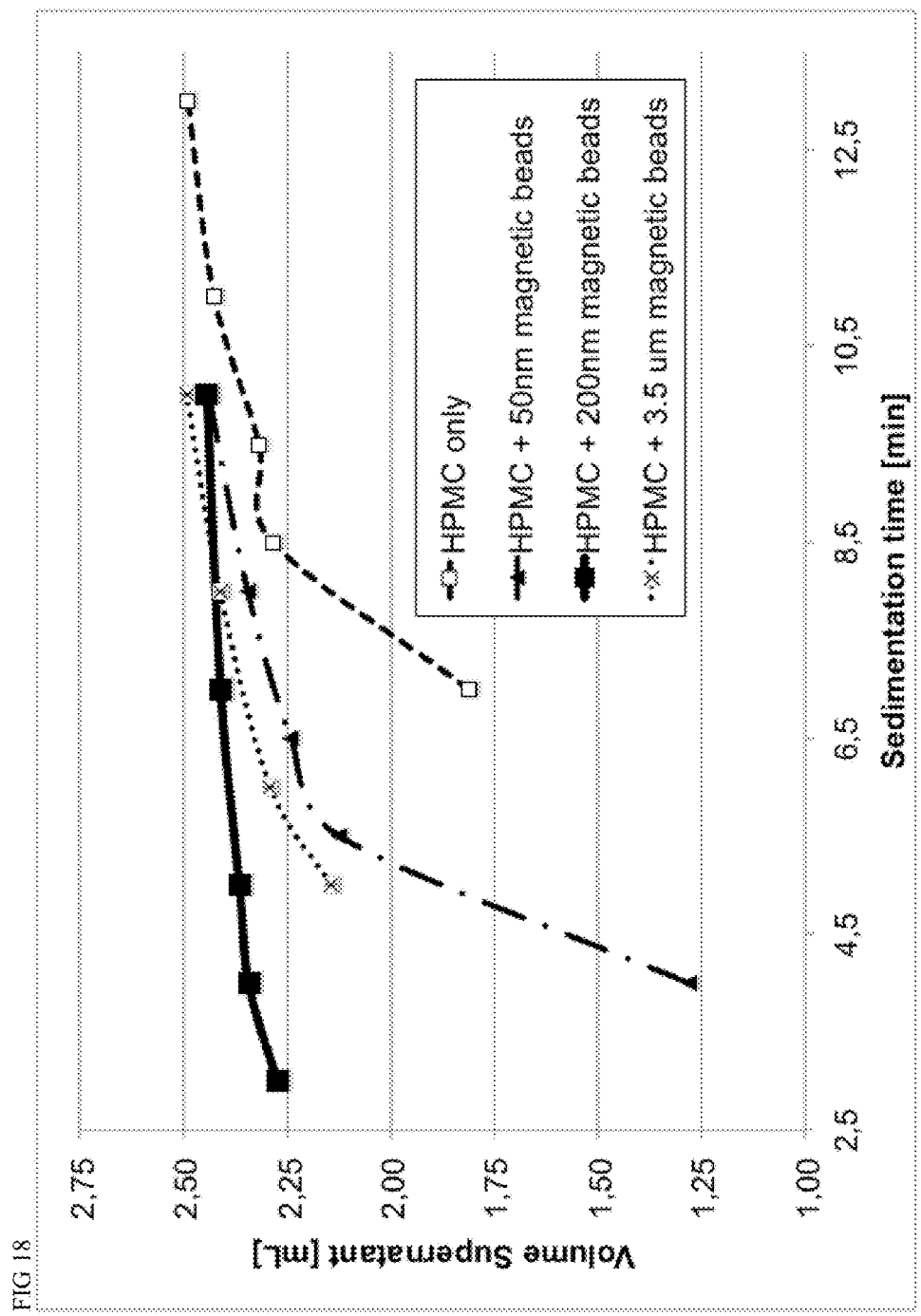

TECHNOLOGY FOR PURIFYING NK CELLS AND OTHER CELL TYPES BY CONCURRENT GRAVITY SEDIMENTATION AND MAGNETIC SEPARATION

RELATED APPLICATIONS

This application is the U.S. National Stage of International Application PCT/EP2012/073083 filed Nov. 20, 2012 and published as WO 2013/076070 on May 30, 2013; which claims priority to EP application 11198050.5, filed Nov. 25, 2011. The PCT application is hereby incorporated herein by reference in its entirety for all purposes.

FIELD OF INVENTION

The present invention relates generally to the field of immunology, in particular to processes and compositions for separation of cells.

BACKGROUND OF THE INVENTION

Cell separation methods are wide spread in scientific and clinical laboratories for research, diagnostics, or clinical applications. Most strategies of cell separation are based on different physical properties such as size and density.

Normally one has to get rid of the erythrocytes before dealing with the cells of interests, the leukocytes. This can be done among other methods by separation of cells using e.g. gradient density centrifugation, peripheral blood mononuclear cells (PBMC) sample preparation or by erythrocyte lysis, all well known methods in the art.

After the elimination of erythrocytes methods using solid phase particles attached to antigen binding moieties, which recognize surface antigens on cells, can be used to separate white blood cells into subpopulations. Such methods may be performed with magnetic beads (e.g. column based MACS technology from Miltenyi Biotec GmbH, Germany; U.S. Pat. No. 5,411,863, U.S. Pat. No. 5,543,289, U.S. Pat. No. 6,020,210, U.S. Pat. No. 6,417,011; or non-column based: Life Technologies, Carlsbad, Calif.) or with non magnetic beads, e.g. with high density beads (U.S. Pat. No. 6,730,230, U.S. Pat. No. 5,576,185, U.S. Pat. No. 6,900,029, U.S. Pat. No. 6,004,743) exploiting gravity sedimentation of dense beads to separate a desired or undesired cell population from a biological sample.

There are a few methods which allow positive selection of cells directly from whole blood, e.g. the use of whole blood micro beads with the MACS technology (Miltenyi Biotec GmbH, Germany). But these methods are limited to small amounts of cells only.

Nonionic polymers such as polysaccharides and synthetic polymers promote red blood cells, i.e. erythrocytes, aggregation when infused in vivo or added to suspensions of erythrocytes in buffer or plasma in vitro. Examples of polymers that induce human RBC aggregation are dextrans of molecular weights 60,000-500,000, polyvinylpyrrolidone of 360,000, and polyoxyethylene (POE) of 20,000.

If anti-coagulated blood is allowed to settle in a tube, erythrocytes sediment ahead of white blood cells, and a leukocyte-rich plasma layer may be removed after 1½ hours or more. The erythrocytes sediment more rapidly than leukocytes because of the spontaneous tendency of erythrocytes to agglomerate. It is possible to accelerate the sedimentation of erythrocytes by adding one of the above mentioned aggregation reagents (Skoog and Beck, 1956, Blood, 11: 436).

Density gradient centrifugation is a technique that allows the separation of cells depending on their size, shape and density. A density gradient is created in a centrifuge tube by layering solutions of varying densities with the dense end at the bottom of the tube. Cells are usually separated on a shallow gradient of sucrose or other inert carbohydrates even at relatively low centrifugation speeds.

Discontinuous density gradient centrifugation is commonly used to isolate peripheral blood mononuclear cells from granulocytes and erythrocytes. For example in a so called Ficoll density separation whole blood is layered over FICOLL-PAQUE®, and then centrifuged. The erythrocytes, granulocytes and approximately 50% of the mononuclear cells settle to the cell pellet while the remaining 50% of the mononuclear cells settle to the Ficoll plasma interface. All density separation techniques have the same basic limitations: they can not separate subpopulations of cells with overlapping density distributions such as lymphocyte subsets and they include time-consuming and laborious centrifugation steps.

Monoclonal antibodies with affinity to cell surface antigens are used for further separation of specific cells after density gradient centrifugation. The antibody-specific technique and the density gradient centrifugation technique can be used simultaneously. Several publications (U.S. Pat. No. 5,840,502, U.S. Pat. No. 5,648,223, U.S. Pat. No. 5,646,004, U.S. Pat. No. 5,474,687 and U.S. Pat. No. 7,316,932) describe the use of dense particles for positive or negative selection by selectively targeting and pelleting desired/undesired cell types using discontinuous density gradient separations.

WO00/73794 discloses a method for separating cells using immunorosettes. The method involves contacting a sample containing nucleated cells and red blood cells with an antibody composition, which allows immunorosettes of the nucleated cells, and the red blood cells to form. The antibody composition contains bifunctional antibodies or tetrameric antibody complexes. The concept here is (1) contacting the sample with an antibody composition comprising (a) at least one antibody that binds to an antigen on the nucleated cells to be separated linked to (b) at least one antibody that binds to the erythrocytes under conditions to allow immunorosettes of the nucleated cells and the erythrocytes to form, and (2) removing the immunorosettes from the sample by centrifugation. Preferably, the antibody specific for the erythrocytes is anti-glycophorin A. Protocols of immunorosetting using Ficoll with and without Hetastarch are described in published manuals of Stem Cell Technologies. The disadvantage of this method is that it includes a time-consuming and laborious centrifugation step.

In U.S. Pat. No. 7,160,723 a method is disclosed which involves for contacting a blood cell-containing sample with a cell separation composition. This composition is i) dextran, ii) anti-glycophorin A antibody, and iii) one or more antibodies against cell surface antigens. In some cases an antibody is substrate-bound to immobilize this molecule. The mixture containing blood cell sample and separation reagent is gently mixed for 30 to 45 minutes. The agglutinated cells are permitted for 30 to 50 minutes to partition away from unagglutinated cells, which remain in suspension. This method suffers from the time-consuming process of more than 1 hour until the desired cell are available for further processing steps. In addition disadvantageously is the rather low recovery of desired cells.

The present invention was made in view of the prior art described above, and the object of the present invention is to provide an improved method for separating desired cells and removing undesired cells from biological samples like whole blood sample, umbilical cord sample, and bone marrow sample.

SUMMARY OF THE INVENTION

The present inventors have developed a magnetically enforced sedimentation method and compositions for separating cells directly from a sample containing erythrocytes, e.g. whole blood. The method and compositions improve the separation of desired cells and the removal of undesired cells from the sample compared to prior art methods, i.e. there is neither the need to first remove the erythrocytes from the sample nor to perform any laborious centrifugation steps of the sample during the process of present invention, resulting in a very fast cell separation method with minimal stress for the cells to be separated. The whole procedure is performed in one single step resulting in an accelerated whole blood cell separation process. The method disclosed herein is faster than methods known in the art resulting in preventing the cells from damage due to limited stress on the cells. In addition, the procedure of the present invention leads to higher recovery and purity of cells compared to methods known in the art.

The cells achieved with the methods and composition of the present invention may be used e.g. to efficiently prepare cells for cell culture, further purification, diagnostic testing or therapeutic administration. Regularly, the desired cells achieved by the present invention are untouched cells, i.e. they are in their natural state. No interaction of the cells with the components of the compositions of the present invention such as antibodies bound to cell surface antigens modifies, e.g. stimulates, the desired cells. In addition, the reduction of separation time needed by the use of the present invention further decreases stress the cells normally are exposed to during processing. Therefore the present invention provides maximal treatment with care to the desired cells making them to minimal stressed cells which are valuable for subsequent applications.

Surprisingly, it was found that the sedimentation of cells in a sample is accelerated if simultaneously (1) the erythrocytes are aggregated by an reagent (e.g. rouleaux-forming agent), i.e. an erythrocyte aggregation reagent such as hydroxypropylmethylcellulose (HPMC) and (2) one or more cellular components, i.e. other blood cells and/or thrombocytes, are bound specifically by magnetic particles, wherein a magnetic field gradient is applied to the magnetic particles, immobilizing the cells bound to the magnetic particles, resulting in a cell pellet and a supernatant phase (liquid fraction). The pellet contains cells sedimented by the erythrocyte aggregation reagent and the magnetic particles which have bound cellular components. The supernatant phase is substantially free of particles and contains the cells that have not been available to sedimentation or immobilization. Generally, these are the desired cells. Therefore, the supernatant phase of the sample can be removed and used for further analysis and/or processing of the desired cells in subsequent steps.

The simultaneous sedimentation and immobilization of cellular components such as erythrocytes and other cells and/or thrombocytes is the response to the forces acting on them. These forces can be due to e.g. gravity sedimentation, centrifugal acceleration and electromagnetism. Each force may act solely or in combination with one or both other forces. Preferentially, the simultaneous sedimentation of the cellular components such as erythrocytes and other cells and/or thrombocytes is performed at 1 to 20×g, more preferentially at 1 to 2×g, most preferentially at 1×g, i.e. with no additional centrifugal acceleration. Gravity sedimentation at 1×g occurs if the container containing the sample to be processed is in an idle state, i.e. no rocking or centrifugation, allowing the particles or cells in the fluid, i.e. the sample with the cellular components, to sediment to the bottom of the container. In any variant, erythrocytes sediment ahead of white blood cells.

It is an advantage of the present invention that there is no need for exerting centrifugal forces for rapid sedimentation of the cells. Preferentially, the method exploits the synergistic effect of applying gravity sedimentation (1×g) and magnetic forces only. Preferentially the magnetic source is positioned to the side of the container containing the sample to be processed. This arrangement results in two forces acting on the cells, one is the gravity sedimentation to the bottom and the other is the magnetic force to the side of the container containing the sample to be processed. But the position of the magnetic source or sources may vary resulting in different directions in which the forces act on the cells.

In addition unexpectedly, it was found that the sedimentation of cells in a sample is accelerated if simultaneously (1) the erythrocytes are aggregated by an erythrocyte aggregation reagent such as HPMC-15 and (2) one or more undesired cellular components are bound specifically by magnetic particles having a size between 100 and 1400 nm, wherein a magnetic field gradient is applied to the magnetic particles, immobilizing the cells bound to the magnetic particles.

In addition surprisingly, it was found that the shape of the cell pellet can be influenced by the selection of the antigen recognizing moiety which is coupled to a magnetic particle and by the choice of the position of the magnetic source relative to the container containing the sample to be processed. If an antigen recognizing moiety, which recognizes a surface protein of one or more undesired cellular components is used, but which does not recognize a surface protein of erythrocytes, the pellet is separated into two parts. Only a slight transition is generated in this case if the magnetic source is positioned on the side of the container containing the sample to be processed as illustrated in FIG. 13. The use of one or more antigen recognizing moieties which recognize a surface protein of erythrocytes and also a surface protein of one or more undesired other cellular components, e.g. CD36, results in a magnetically enforced sedimentation of all cellular components which are desired to be sedimented and/or immobilized. If the magnetic source is positioned in the same way as shown in FIG. 13 the pellet forms under such conditions a different shape, resembling an exponential function curve resulting in a smooth transition as illustrated in FIG. 14. This or similar shapes of pellets are advantageous for removing the supernatant if e.g. a pipette is used resulting in an increased volume of the supernatant which can be recovered (Example 27).

The compositions of the present invention comprise i) an erythrocyte aggregation reagent and ii) a set of one or more mono- and/or multi-specific magnetic particles with at least one antigen recognizing moiety coupled to the particles, wherein said particles with said at least one antigen recognizing moiety specifically bind to at least one antigen specific for one or more undesired cellular components.

BRIEF DESCRIPTION OF THE DRAWINGS

FIG. 8: Magnetic beads have been conjugated to antibodies of multiple specificities and depletion performance has been evaluated according to protocols described in Examples 1, 2 and 3.

FIG. 16: Design of a magnet yoke to hold 2 cuboid rare earth magnets (88*24*10 mm). The centrifuge tube can be placed between the perpendicularly oriented magnets for cell separation.

FIG. 17: Design of a magnet yoke to hold 1 cuboid rare earth magnet (88*24*10 mm), position of the magnet and the 50 ml centrifuge tube.

FIG. 18: Results of an experiment determining sedimentation speed of combination of HPMC-15 with different sizes of antibody cocktail conjugated magnetic beads (Example 26)

DEFINITIONS

Figure 1:
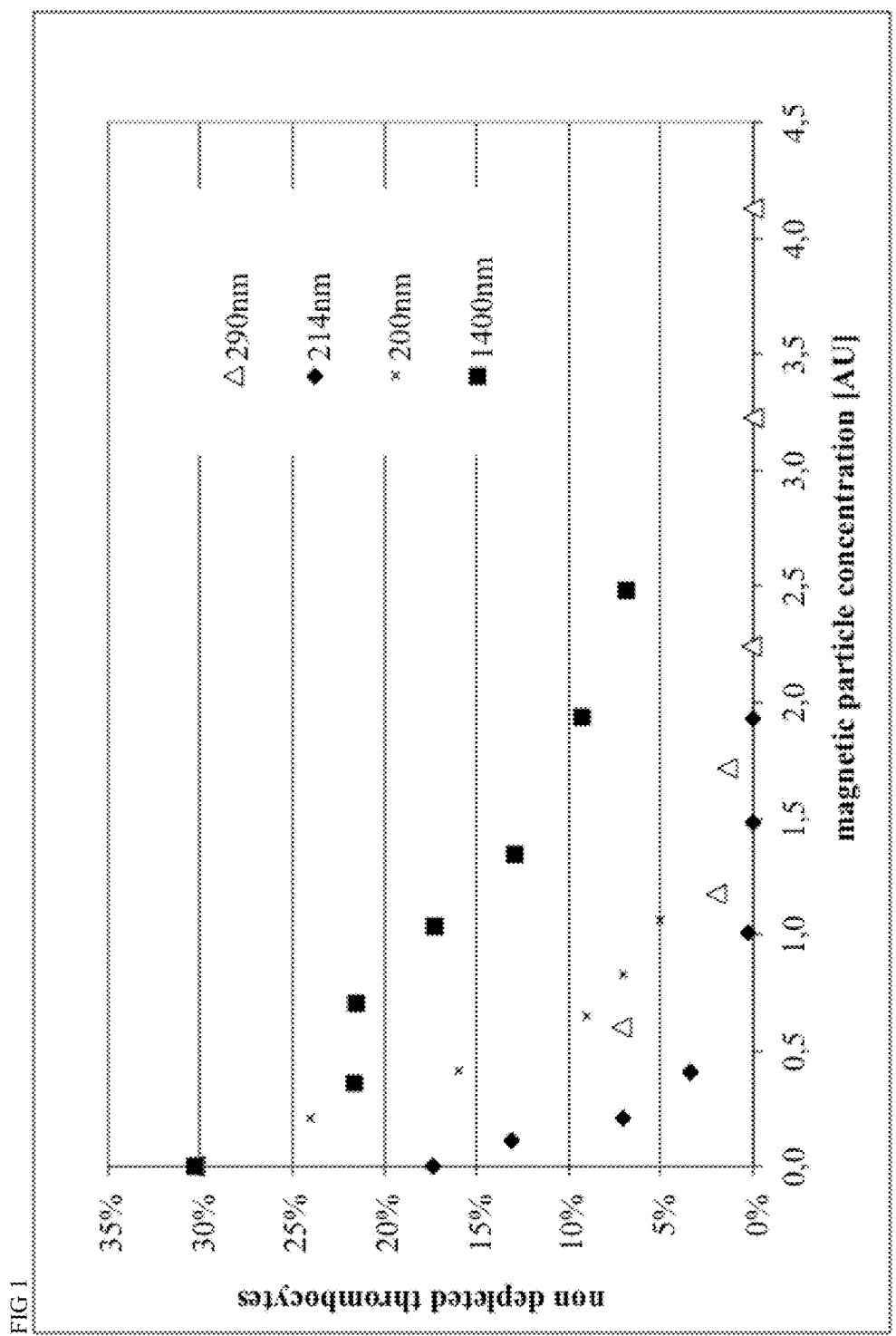
FIG. 1: Thrombocyte depletion efficiency of magnetic beads of different size conjugated to monoclonal antibodies CD61 and CD15 in a 1:1 ratio
Figure 2:
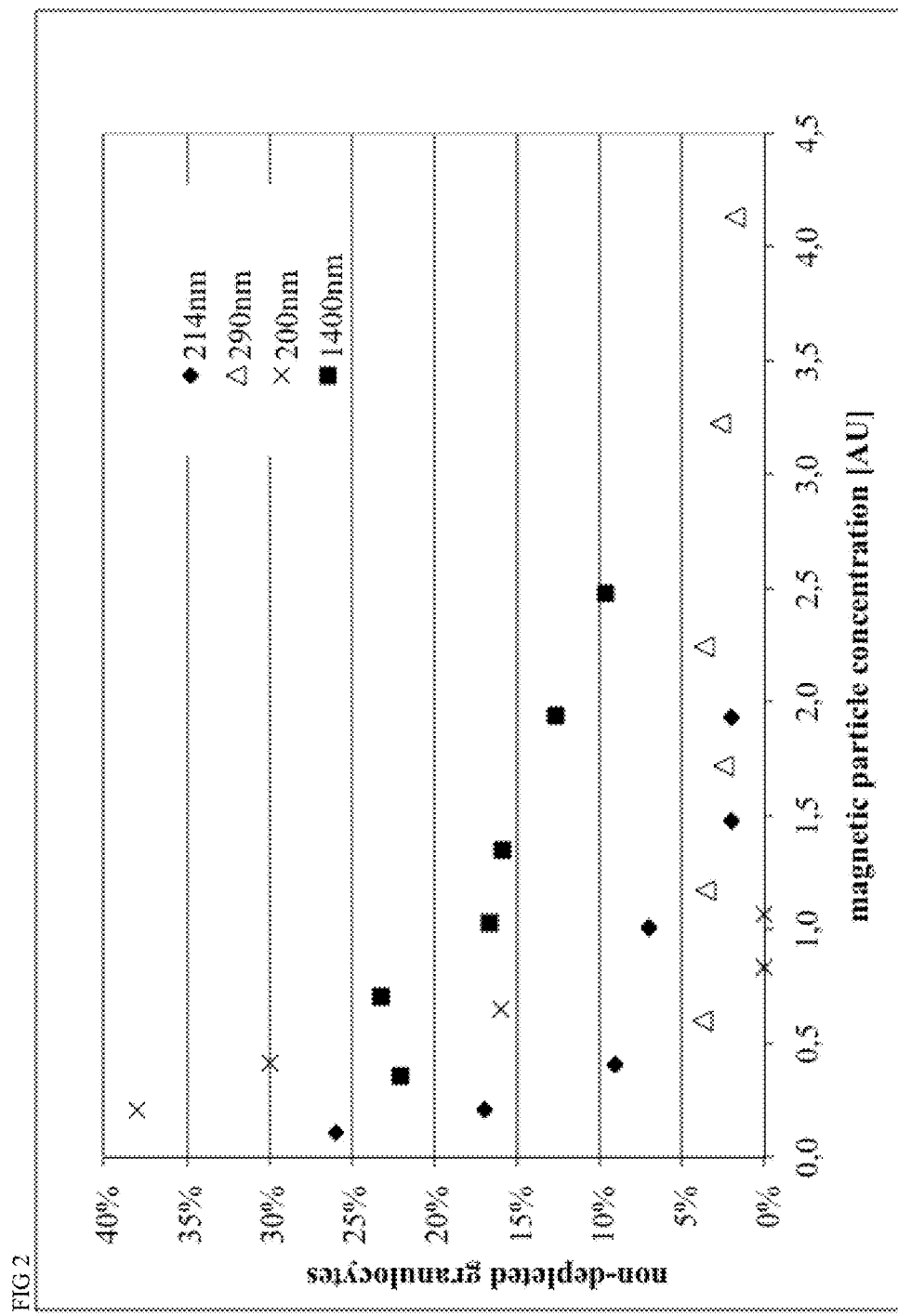
FIG. 2: Granulocyte depletion efficiency of magnetic beads of different size conjugated to monoclonal antibodies CD61 and CD15 in a 1:1 ratio
Figure 3:
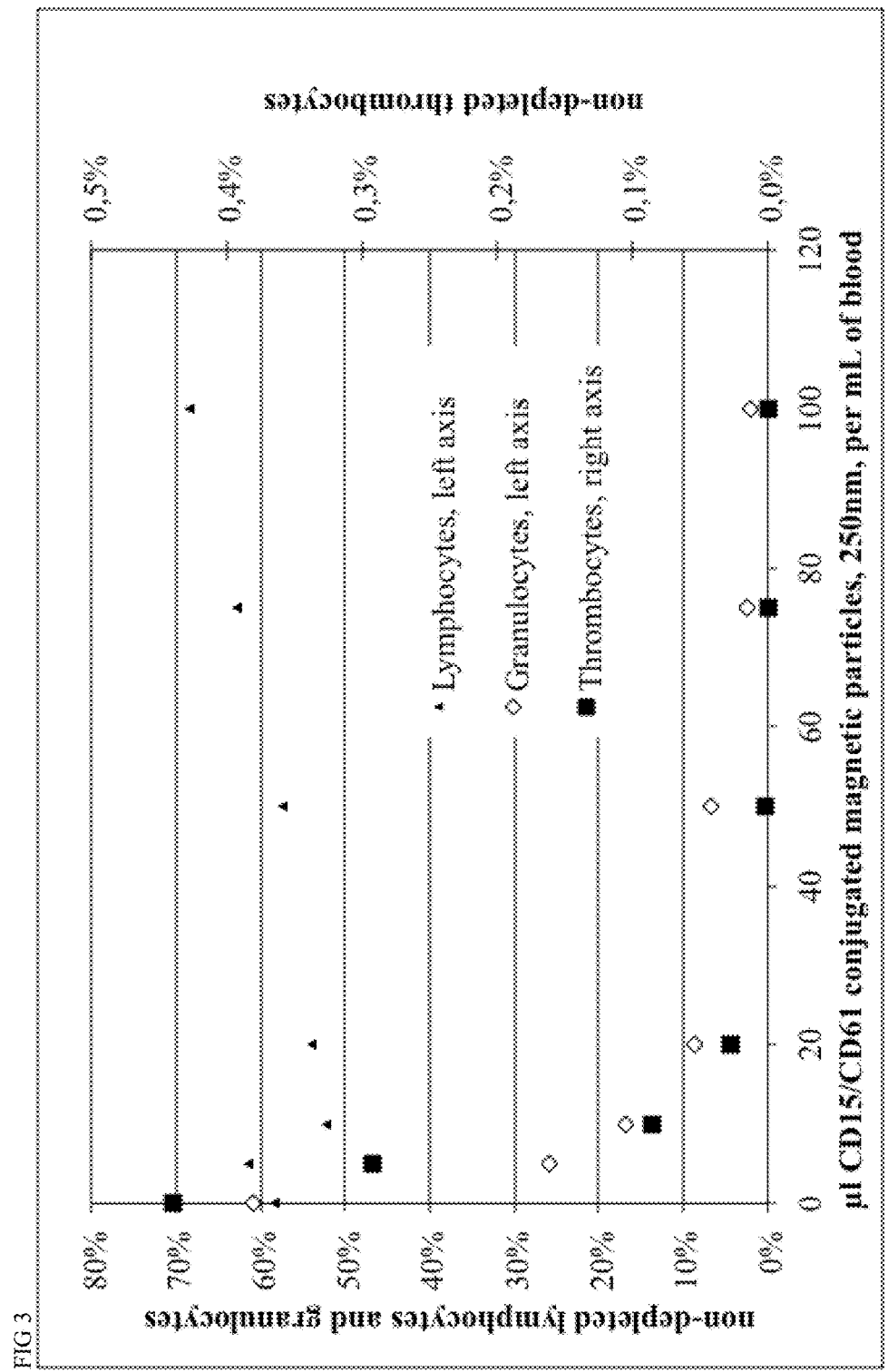
FIG. 3: Granulocyte and thrombocyte depletion efficiency of 250 nm magnetic beads conjugated to monoclonal antibodies CD61 and CD15 in a 1:1 ratio
Figure 4:
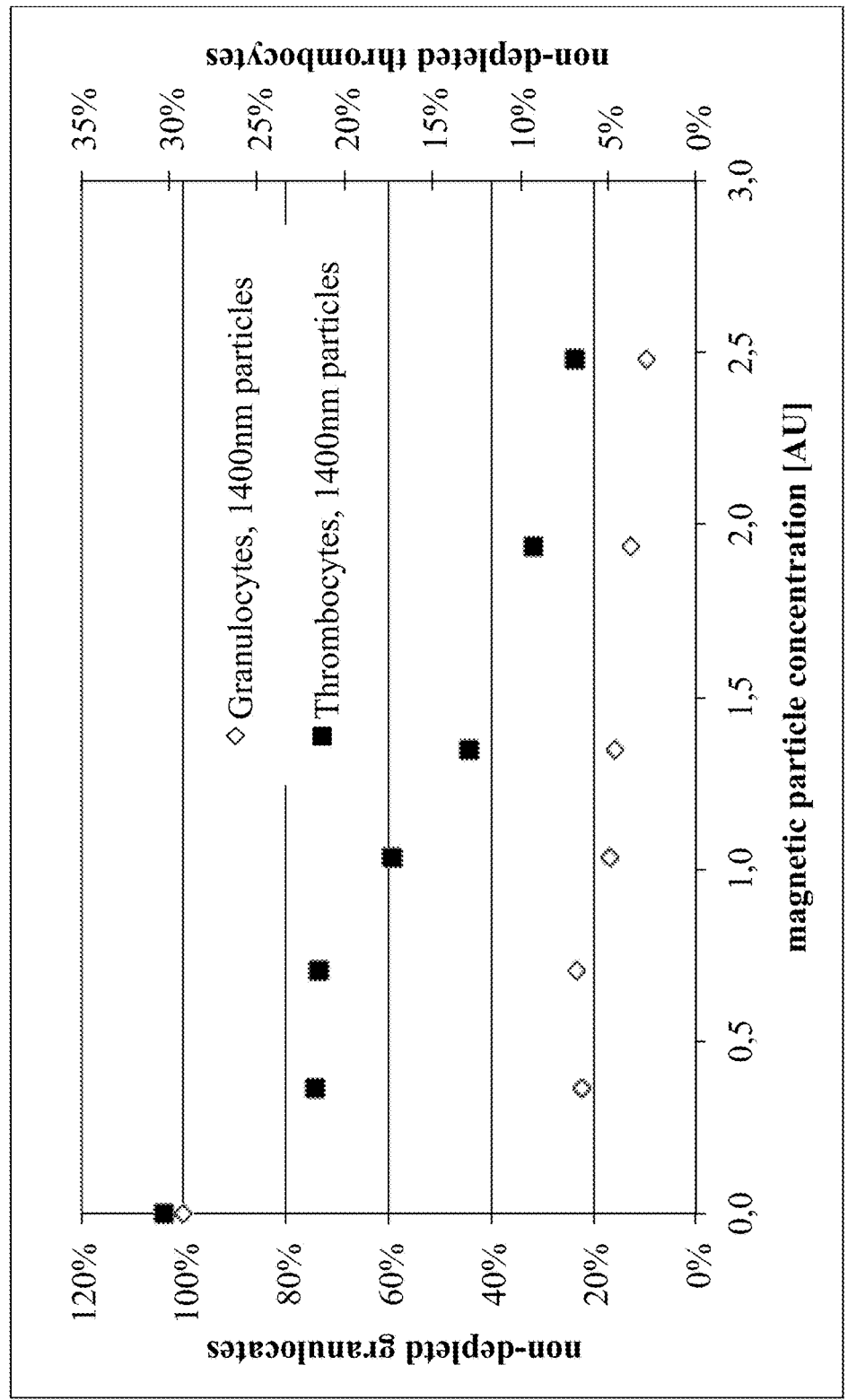
FIG. 4: reduced granulocyte and thrombocyte depletion efficiency of 1400 nm magnetic beads conjugated to monoclonal antibodies CD61 and CD15 in a 1:1 ratio

Unless defined otherwise, technical and scientific terms used herein have the same meaning as commonly understood by one of ordinary skill in the art to which this invention belongs.

The term "cellular components" as used herein refers to cells which are common in a whole blood sample, peripheral blood sample, leukapheresis sample, buffy coat sample, umbilical cord sample, and bone marrow sample, including e.g., erythrocytes, leukocytes and platelets. Especially the leukocytes consist of many subpopulation of cells such as e.g. T-cells, regulatory T-cells, B-cells, NK cells, dendritic cells, monocytes, granulocytes, hemapoetic stem cells.

The term "particle" as used herein refers to a solid phase such as colloidal particles, microspheres, nanoparticles, or beads. Methods for generation of such particles are well known in the field of the art. The particles are magnetic particles in the present invention. The particles may be in a solution or suspension or they may be in a lyophilized state prior to use in the present invention as shown in the example 16. The lyophilized particle is then reconstituted in convenient buffer before contacting with the sample to be processed regarding the present invention. Preferentially, the particle may have a size in diameter of at minimum 100 nm and at maximum 1400 nm, more preferentially, the particles have a size of 200 to 500 nm in diameter. At least one antigen recognizing moiety is coupled to a magnetic particle wherein said particle with said at least one antigen recognizing moiety specifically bind to at least one antigen specific for cellular components.

The term "magnetic" in "magnetic particle" as used herein refers to all subtypes of magnetic particles which could be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

The term "erythrocyte aggregation reagent" as used herein refers to any molecule known in the art which triggers red blood cell aggregation within a blood cell-containing sample. Preferentially, the erythrocyte aggregation reagent is selected from the group consisting of high-molecular weight proteins (e.g. fibrinogen and immunoglobulins) and non-ionic polymers such as polysaccharides and synthetic polymers. More preferentially, the erythrocyte aggregation reagent is a non-ionic polymer selected from the group consisting of dextran, hydroxyethyl starch, polyvinyl pyrrolidone (PVP), methylcellulose or hydroxypropylmethylcellulose (HPMC). Most preferentially, the erythrocyte aggregation reagent is HPMC-15.

The term "antigen-recognizing moiety" as used herein refers to an antibody or antigen-binding fragment. The term "antibody" as used herein refers to polyclonal or monoclonal antibodies. The antibodies may also be modified antibodies (e.g. oligomers, reduced, oxidized and labelled antibodies). The term "antibody" comprises both intact molecules and antibody fragments, such as Fab, Fab+, F(ab')2, Fv and single-chain antibodies. Additionally, the term "antigen-binding fragment" includes any moiety that binds preferentially to the desired target molecule of the cell to be sedimented within this method. Suitable moieties include, without limitation, oligonucleotides known as aptamers that bind to desired target molecules (Hermann and Pantel (2000) Science 289: 820-825), carbohydrates, lectins or any other antigen binding protein (e.g. receptor-ligand interaction).

The terms "mono-specific particle" and "multi-specific particle" as used herein refer to the coupling of one antigen recognizing moiety to a particle in the case of a mono-specific particle and two or more antigen recognizing moieties to a particle in the case of a multi-specific particle, respectively. The two or more antigen recognizing moieties, e.g. different antibodies, of the multi-specific particle preferentially bind to antigens specific for different subpopulations of cells, respectively. In the following, "mono-specific particles" and "multi-specific particles" are referred to by the antigen recognizing moieties they are coupled with. For example, a particle bound to antibodies against the antigens CD61 and CD15 is referred t as "CD61, CD15, particle".

The anti-CD61 antibody binds to platelets and CD15 binds to granulocytes, i.e. the multi-specific particle binds two subpopulations of cells. The linkage between antibody and particle can be covalent or non-covalent. A covalent linkage can be, e.g. the linkage to carboxyl-groups on polystyrene beads, or to NH2 or SH2 groups on modified beads. A non-covalent linkage is e.g. via biotin-avidin as shown in Example 12 or a fluorophore-coupled-particle linked to anti-fluorophore antibody.

The term "sample" as used herein refers to an erythrocytes containing sample, e.g. peripheral blood sample, leukapheresis harvest, buffy coat preparation, umbilical cord sample, and bone marrow aspirate as shown exemplary in Example 13. The samples can be from animals, especially mammals. Preferably, the samples are from humans.

The term "cell modification agent" as used herein refers to e.g. cell stimulation agents like cytokines, antibodies or peptides. In addition, cell modification agents can be antibodies coupled to magnetic beads, e.g. superparamagnetic beads, for subsequent cell separation, using e.g. MACS technology. A further cell modification agent is a fluorochrome-coupled antibody, which can be used subsequent to the cell separation of the present invention for cell analysis. Alternatively, the magnetic beads, e.g. superparamagnetic beads, which are conjugated with a cell modification reagent, e.g. an antibody, may be given to the final cell composition after using the present invention for a further cell separation, using e.g. MACS technology (see Example 25).

The term "pellet" or "cell pellet" as used herein refers to the non-liquid phase as a result of the present invention. The pellet consists of the erythrocytes sediment (generated at least partly by gravity sedimentation as a result of applying the erythrocyte aggregation reagent in the sample) and the immobilized magnetic particles containing at least partly cellular components (as a result of applying a magnetic field gradient to the sample). The pellet or cell pellet is the entity of all pellets generated by sedimentation of cells and immobilization of cells by magnetic forces within the container containing the sample to be processed using the method of the present invention. If an antigen recognizing moiety which recognize a surface protein of erythrocytes but also a surface protein of one or more other cellular components is used in the present invention then the erythrocytes also are immobilized by magnetic particles. Dependent on the position of the magnet the shape of the pellet may vary, from one close pellet over a smooth transition of two pellets to two or even more separated pellets. If two or more pellets are present due to the arrangement of the magnetic sources the term pellet as used herein refers to all pellets, i.e. the pellet is the sum of all part pellets within a container generated by applying the present invention. The magnetic particles accumulate near the surface closest to the magnetic field gradient source, i.e. the magnet. The particles are the mono- or multi-specific particles of the present invention and therefore a part of the particles in the pellet may have cells attached, another part may be free of cells.

The term "supernatant" or "supernatant phase" as used herein refers to the liquid phase as a result of the present invention, in contrast to the pellet. The supernatant phase consists of all cell components which are not part of the aggregation complexes generated by the present invention. Which subsets of cells do not aggregate can be selected by selecting the specificity of the mono- or multi-specific particle used in the present invention. Regularly, the cells of the supernatant phase are untouched cells and are the desired cells, i.e. the target cells, of the separation process.

The term "target cells" as used herein refers to the cells which are the desired cells separated by the present invention. The terms "target cells" and "desired cells" are interchangeable and have the same meaning regarding the present invention. Regularly, the target cells are the untouched cells of the supernatant generated by the process of the present invention. The selection of desired cells, i.e. the target cells, which are in the supernatant, can be defined by the selection of antigen recognizing moieties used in the process of the present invention. Regularly, the target cells have no antigen for the antigen recognizing moieties coupled to the particle(s) used in the process of the present invention.

The term "undesired cells" as used herein refers to the cells which are specifically bound by at least one antigen recognizing moiety which is coupled to a magnetic particle of the present invention. These cells form part of the pellet generated by the present invention.

DETAILED DESCRIPTION OF THE INVENTION

The present invention provides methods and compositions for isolating, enriching and/or purifying cells from a sample containing erythrocytes.

The sedimentation of cells from a blood cell containing sample is accelerated by the present invention compared to methods known in the art. This is surprisingly achieved by the simultaneous separation of the erythrocytes which are aggregated in the presence of an erythrocyte aggregation reagent and the separation of other undesired cellular components which sediment and immobilize in the presence of mono- and/or multi-specific magnetic particles, which have specificities for one or more undesired cellular components, respectively.

The erythrocyte aggregation reagent is responsible for the generation of the aggregate formation of the erythrocytes and of some platelets, i.e. thrombocytes, resulting in the sedimentation of the erythrocytes and thrombocytes. The magnetic particle is responsible for the aggregation of undesired cellular components in a magnetic field gradient, which are recognized by this particle resulting in the immobilization of the mono- and/or heterotypic agglutination of these cells. The magnetic field gradient is generated by a magnetic source, e.g. by a permanent magnet or electromagnet. The two aggregation complexes positively interfere and result in fast sedimentation and/or immobilization of both aggregation complexes.

It is within the scope of the invention that the steps of the present invention regarding to gravity sedimentation and immobilization of the magnetic particles by the magnetic forces generated by a magnetic source applied the container containing the sample to be processed may be performed in two separated steps. But the simultaneous performance of these two steps is strongly preferred due to exploiting the synergistic effects resulting in optimal results, i.e. purity, and in saving time for the separation procedure.

Therefore, it is an object of the present invention to provide a method for enriching and/or recovering desired cells from a sample containing the desired cells, erythrocytes and undesired cells comprising:
   a) contacting the sample with a composition, said composition comprising:
      i) an erythrocyte aggregation reagent
      ii) at least one antigen recognizing moiety coupled to a magnetic particle, wherein said particle with said at least one antigen recognizing moiety specifically binds to at least one antigen specific for one or more undesired cellular components; and optionally
      iii) one or more cell modification agents, which modifies the desired cells;
   b) applying simultaneously
      i) gravity sedimentation for sedimentation of erythrocytes; and
      ii) a magnetic field gradient to said sample for immobilizing said magnetic particle generating a pellet and a supernatant phase, and
   c) recovering the desired cells from the supernatant phase.

In addition surprisingly, it was found that the size of the particles used in the present invention has a further impact on the present invention. It was found that the sedimentation of cells in a sample is accelerated if simultaneously (1) the erythrocytes are aggregated by an erythrocyte aggregation reagent such as HPMC-15 and (2) one or more undesired cellular components are bound specifically by magnetic particles having an average size in diameter between 100 and 1400 nm, preferentially between 200 and 500 nm, wherein a magnetic field gradient is applied to the magnetic particles, immobilizing the cells bound to the magnetic particles. The use of particles having an average size between 100 and 1400 nm, preferentially between 200 and 500 nm, in the present invention results in a further superior separation of cells compared to smaller or larger particles, respectively (Example 1).

Figure 6:
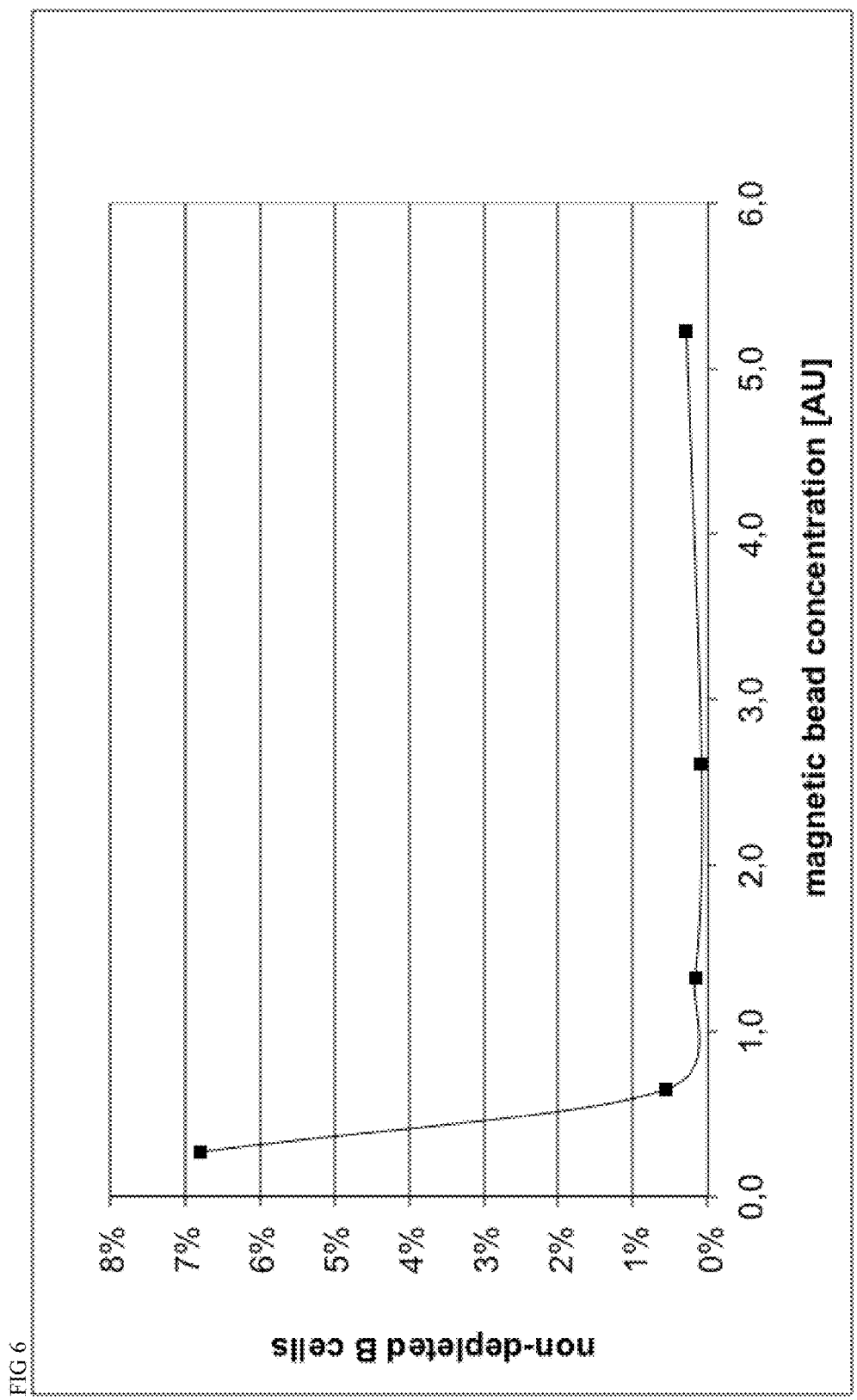
FIG. 6: B cell depletion efficiency of conjugates of 240 nm magnetic particles conjugated to CD19 antibody
Figure 7:
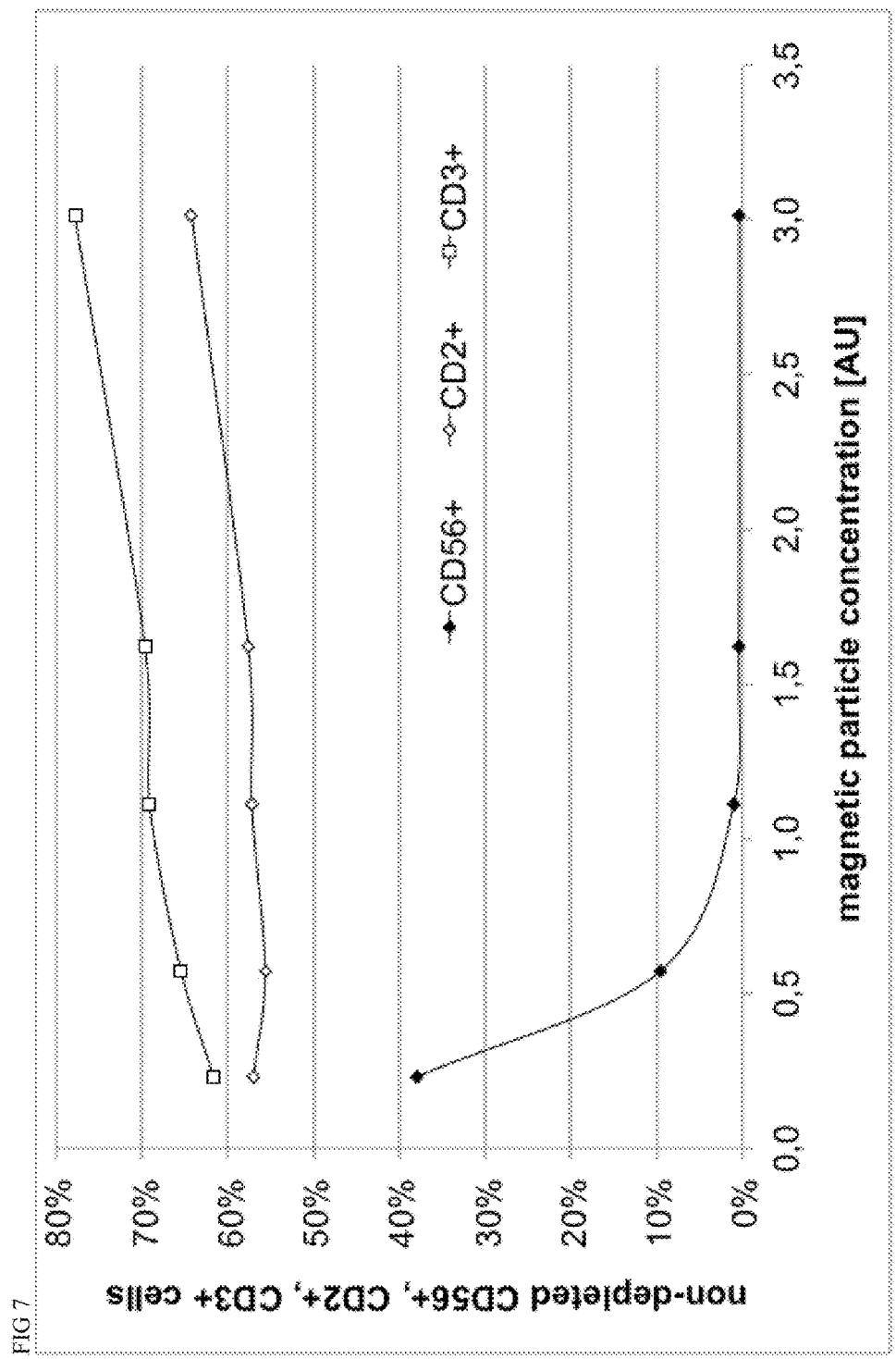
FIG. 7: NK cell depletion efficiency of conjugates of 240 nm magnetic particles conjugated to CD56 antibody
Figure 9:
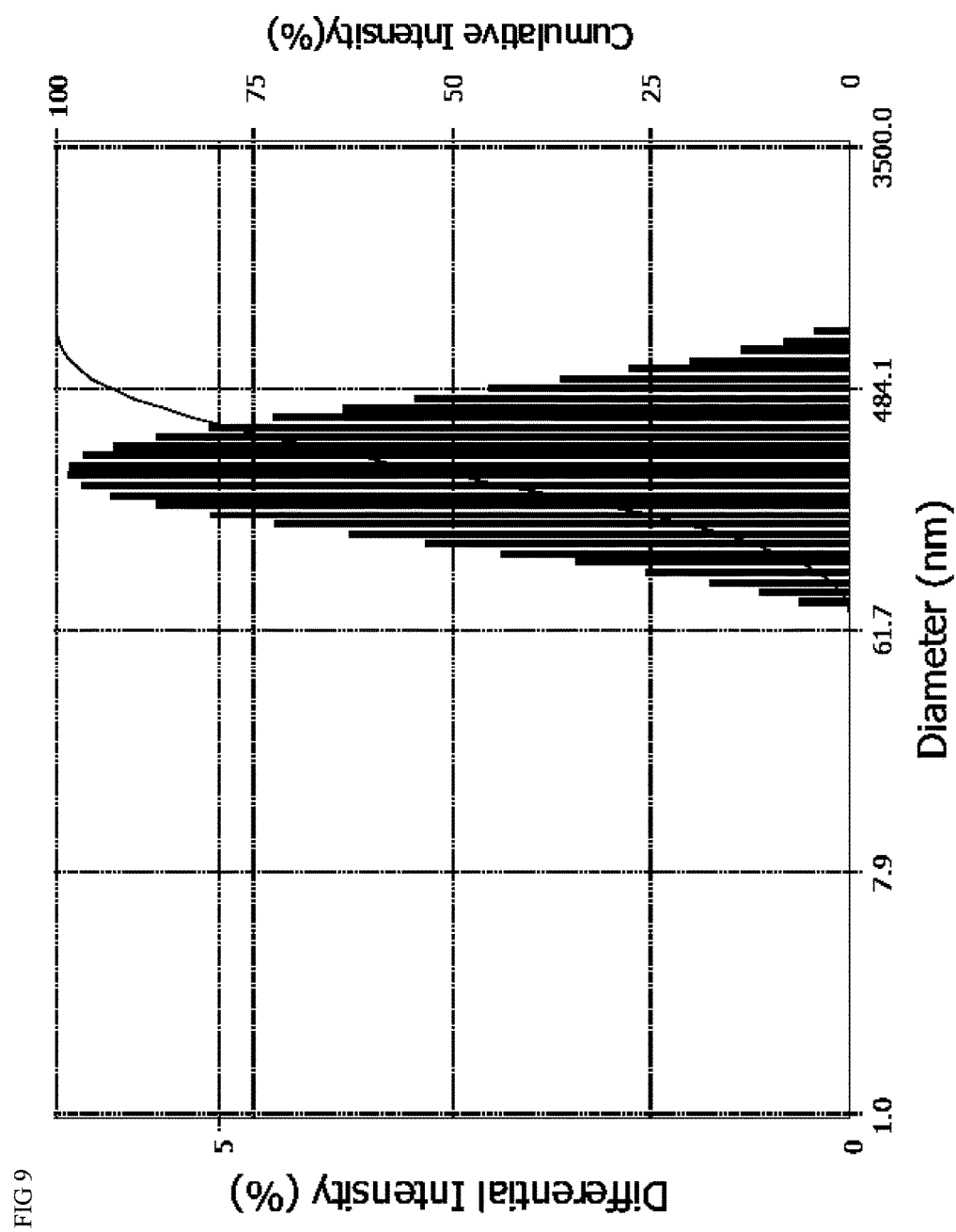
FIG. 9: The size of a conjugate of magnetic particles conjugated to a CD56 antibody has been determined by measurement on a Beckman Coulter Delsa Nano instrument.
Figure 12:
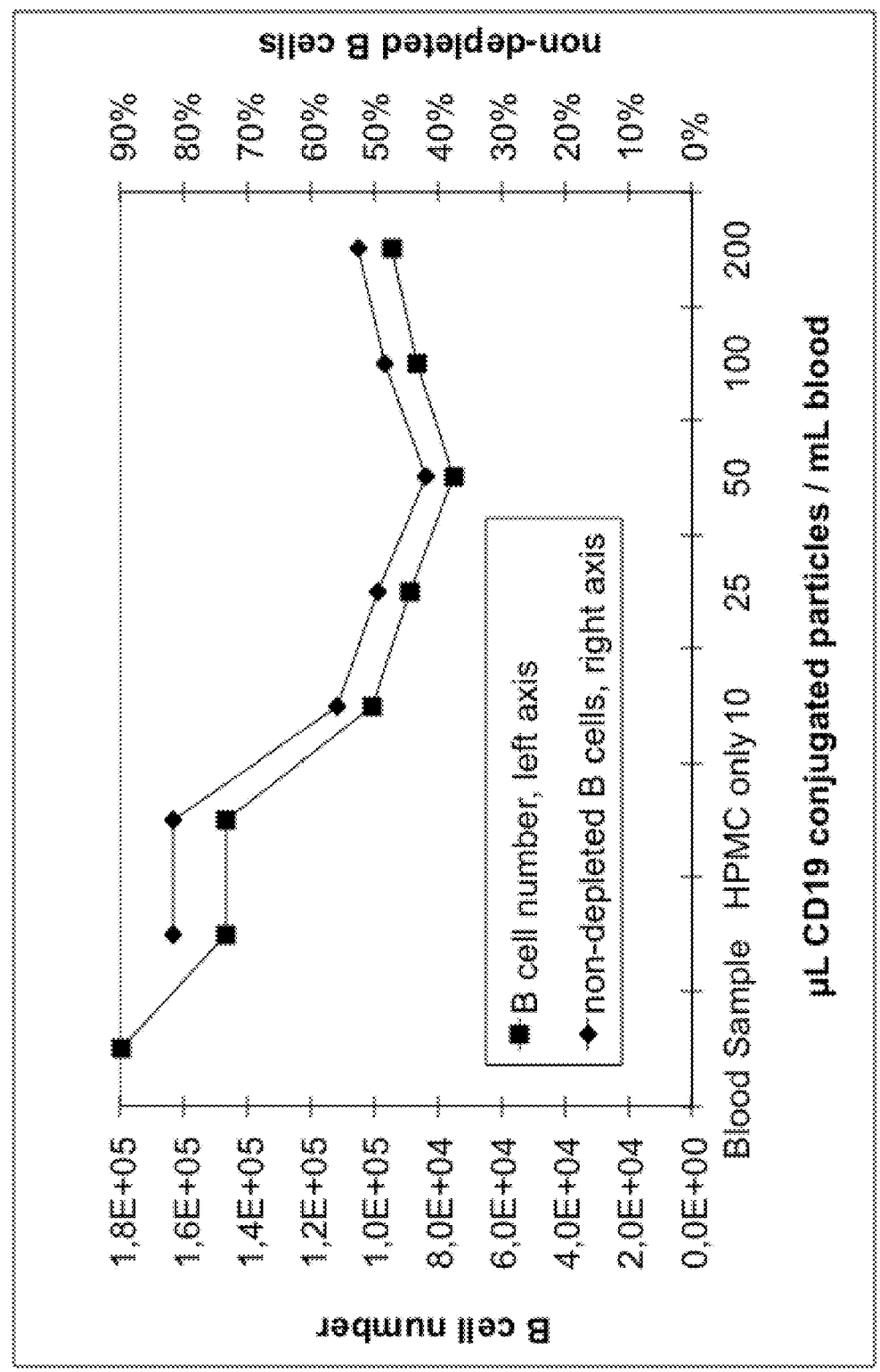
FIG. 12: Unsufficient separation efficiency of an CD19 antibody conjugated to 50 nm magnetic particles

Small magnetic particles of 50 nm average diameter have a reduced impact on accelerating erythrocyte sedimentation than 200 nm particles (FIG. 18) and result in a suboptimum depletion efficiency for some antibodies conjugated to (CD19, FIG. 12). Particles with an average diameter of 260 nm to 290 nm showed good depletion efficiency when conjugated to all antibodies evalated (examples see FIG. 6 and FIG. 7) and had a size distribution that about 95% were in the range of 100 nm to 1400 nm and about 90% in the range of 200 nm to 500 nm (FIG. 9). Particles with an average size in diameter of more than 1400 nm showed unsufficient depletion efficiency for granulocytes and thrombocyte when conjugated to CD15 and CD61 antibodies.

It is not necessary to include an antigen-recognizing moiety, which solely recognizes a surface protein of erythrocytes such as anti glycophorin A in the present invention. Using an antigen recognizing moiety solely directed against a surface protein of erythrocytes such as anti glycophorin A antibodies have neither a positive nor a negative effect in the present invention, in contrast to the disclosure of the methods in WO00/73794 and U.S. Pat. No. 7,160,723 (Example 15).

Further surprisingly, it was found that the shape of the cell pellet generated by the present invention can be influenced by two parameters, i) the selection of the antigen recognizing moiety which is coupled to a magnetic particle and ii) the choice of the position of the magnetic source relative to the container containing the sample to be processed.

Figure 15:
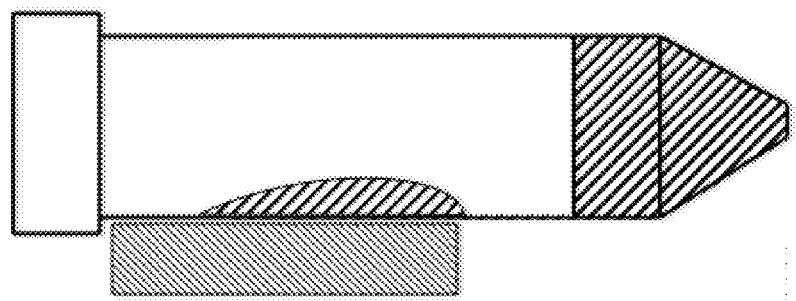
FIG. 15: The pellet breaks into two parts, when the magnet is placed distant from the bottom of the tube. The upper pellet contains magnetically labelled cells attracted to the magnet. The lower pellet contains aggregates (erythrocytes, thrombocytes, cell aggregates) with no or weak magnetic labelling.
Figure 14:
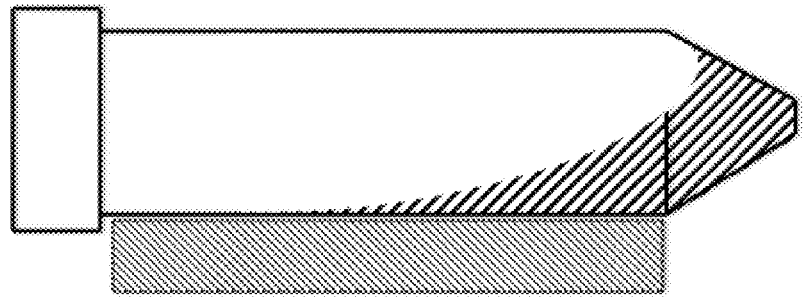
FIG. 14: The pellet of erythrocytes and magnetically labelled cells form a different shape, compared to the situation in FIG. 13, when antibodies both binding to erythrocytes and other undesired cellular components, i.e. non-target leukocytes, are used such as CD36.
Figure 13:
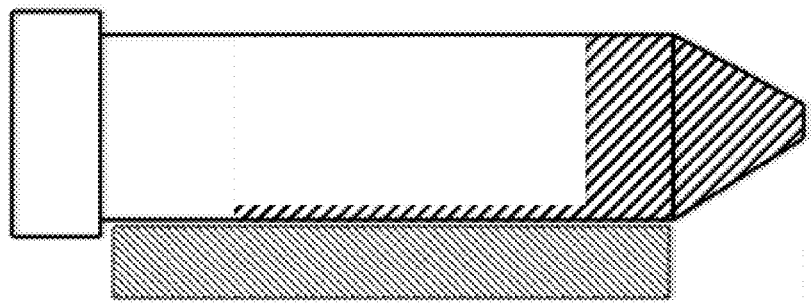
FIG. 13: Shape of the pellet when antibody cocktails without CD36 or other antigen recognizing moieties which do not recognize surface proteins of erythrocytes but of other undesired cellular components are used. The pellet consists of two parts. The upper part contains magnetically labelled cells attracted to the magnet. The lower part contains aggregates (erythrocytes, thrombocytes, cell aggregates) with no or weak magnetic labelling, separated by sedimentation.

If an antigen recognizing moiety, which recognizes a surface protein of one or more undesired cellular components is used, but which does not recognize a surface protein of erythrocytes, the pellet is separated into two parts. Only a slight transition is generated in this case if the magnetic source is positioned on the side of the container containing the sample to be processed as illustrated in FIG. 13. In contrast thereto, the use of one or more antigen recognizing moieties which recognize a surface protein of erythrocytes but also a surface protein of one or more other undesired cellular components, i.e. non-target leukocytes, has an impact of the shape of the cell pellet. Such markers, which recognize surface proteins on erythrocytes and other cellular components, are e.g. CD35, CD36, CD44, CD45RB, CD47, CD49e, CD55, CD58, CD59, CD75, CD75S, CD99, CD108, CD111, CD139, CD147, CD220, and CD222. The use of such an antigen recognizing moiety, e.g. CD36, results in a magnetically enforced sedimentation of all cellular components which are desired to be sedimented. If the magnetic source with the magnetic field gradient is positioned on the side of the container containing the sample to be processed as illustrated in FIG. 14 the pellet is shaped similar to an exponential function curve. But generally, the pellet may form different shapes depending on the position of the magnetic source. The shape of the cell pellet obtained by the method of the invention is a result of the forces acting on the cells. The erythrocytes sediment partly due to gravity and partly due to magnetism. The erythrocytes are magnetized if one or more antigen recognizing moieties, which recognize a surface protein of erythrocytes but also a surface protein of one, or more other undesired cellular components are used in the present invention. Therefore, if the magnet is positioned nearly to the bottom of the container containing the sample to be processed as illustrated in FIG. 14, a smooth transition of the two types of cell pellets, i.e. one cell pellet generated by gravity sedimentation and the other pellet generated by magnetic forces, is generated. This or similar shapes of pellets are advantageous for removing the supernatant if e.g. a pipette is used. This shape of pellet allows for easier and more complete removal of the non-pellet phase, i.e. the supernatant phase which contains regularly the desired cells. But the magnetic field gradient may be oriented in any position relative to the container containing the sample to be processed resulting in different forms of the pellets. If the magnet is positioned more distantly from the bottom of the container containing the sample to be processed two separated pellets are generated as illustrated in FIG. 15. The upper pellet contains cells which are strongly magnetized due to the labelling with the magnetic particles. If an antigen recognizing moiety which recognizes surface proteins on erythrocytes is used this pellet contains erythrocytes and other undesired cellular components. If no antigen recognizing moiety which recognizes surface proteins on erythrocytes is used this pellet contains other undesired cellular components but no erythrocytes. The lower pellet contains cells which are weaker magnetized due to the labelling with the magnetic particles, i.e. mostly the remaining erythrocytes.

Therefore, in another embodiment of the present invention, the magnetic particle is provided with at least one antigen recognizing moiety which recognizes an antigen on the cell surface of erythrocytes and in addition an antigen of at least one other undesired cellular component The use of a magnetic source at the bottom of the container containing the sample to be processed is not preferred. This results in a higher distance the magnetic aggregates have to be moved, i.e. 10 cm (tube height) compared to 3 cm (tube diameter).

The present invention utilizes a magnetic field gradient generated by a magnetic source, e.g. by a permanent magnet or electromagnet. Any type and form of magnet can be used within the present invention, like the MACSiMAG™ Separator commercially available by Miltenyi Biotec GmbH, Germany. Different magnet designs have been evaluated with the present invention. The MACSiMAG™ separator has also been modified with higher magnets to attract magnetic particles and magnetically labelled cells to the wall of the tube over the complete height of the tube. Commercially available magnets for 50 ml centrifuge tubes have been evaluated including a magnet from SensScreen Technologies (Germany) and from Stem Cell Technologies ("Easy 50" Easy Sep Magnet). Magnetic aquarium glass cleaners have been evaluated for the present invention. These cleaners consist of strong permanent magnets combined with a magnetic yoke, embedded in a plastics housings and having a cleaning material attached to the surface of the inner magnet to clean the aquarium glass. Several designs have been developed for use of cuboid permanent rare earth magnets with a size of 88 mm*24 mm*10 mm in different magnet yoke, including U shaped yokes and perpendicular yokes (see FIG. 16 and FIG. 17). Halbach arrays also have been successfully used with the present invention.

In addition to magnets placed outside the wall of the tube magnets may also be immersed into the tube, either cylindrical, cuboid or spherical.

It is a further object of the invention to provide compositions for isolating, enriching and/or recovering therapeutically or diagnostically or scientifically valuable cells from e.g. peripheral blood, umbilical cord blood, and bone marrow.

The composition according to the invention comprises
i) an erythrocyte aggregation reagent
ii) a set of one or more mono- and/or multi-specific magnetic particles with at least one antigen recognizing moiety coupled to the particles, wherein said particles with said at least one antigen recognizing moiety specifically bind to at least one antigen specific for one or more undesired cellular components; and optionally
iii) one or more cell modification agents, which modify the desired cells.

A cell separation composition in accordance with the invention comprises an erythrocyte aggregation reagent and one or more mono- and/or multi-specific magnetic particles. The specificity of the particles is for an antigen of a cell to be sedimented or immobilized, i.e. an undesired cell. Cell separation compositions contain antigen recognizing moieties, e.g. antibodies, against blood cell surface antigens including, e.g. CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, anti Fc_epsilon, anti T cell receptor alpha/beta, anti T cell receptor gamma/delta, anti Biotin, anti IgE, anti HLA-DR and combinations thereof.

Preferable, the magnetic particles of said composition have a average diameter in size between 100 and 1400 nm, preferentially between 200 and 500 nm.

Such compositions may comprise one type of mono- or multi-specific particle, or may comprise more than one mono- or multi-specific particles or a mixture of mono- and multi-specific particles. A composition convenient for separating untouched cells of a specific subpopulation of cells should comprise antigen recognizing moieties coupled to a magnetic particle wherein such antigen recognizing moieties do not recognize the subset of cells, which are the cells of interest, i.e. the desired cells or target cells which should remain untouched. E.g. an antigen recognizing moiety against CD61, CD62, CD41, respectively, can be used if platelets are desired to be removed from the supernatant. Antigen recognizing moieties against CD66b, CD15, CD16, respectively, can be used if granulocytes are desired to be removed. CD14, CD33, respectively, can be used if monocytes/macrophages are desired to be removed. CD19, CD20, respectively, can be used if B cells are desired to be removed. CD3, CD4, CD8, T cell receptor alpha/beta, respectively, can be used if T cells are desired to be removed. CD56, CD335, respectively, can be used if NK cells are desired to be removed.

Generally the use of one antigen recognizing moiety, e.g. an antibody, coupled to the particles results in consistent separation of the desired cells within the present invention (Example 2). The use of two or more antigen recognizing moieties, e.g. antibodies, coupled to the particles, preferentially to particles of average size in diameter between 100 and 1400 nm, more preferentially between 200 and 500 nm, results in a superior separation of the desired or undesired cells compared to the prior art methods (see Example 3).

The use of at least one antigen recognizing moiety, e.g. antibody, coupled to the particles within the present invention includes—but is not limited to—particles coupled with 2, 3, 4, 6, 8, 10 or 12 antigen recognizing moieties, e.g. antibodies, respectively, resulting in equivalent or even superior separation properties of these particles as shown in Example 3.

The ratio of different antigen recognizing moieties, e.g. antibodies, coupled to a particle may vary. Preferentially, the ratio is between 1:1 and 1:50, more preferentially between 1:1 and 1:20 (see Example 3). If additional antigen recognizing moieties are coupled to the particle than every additional antigen recognizing moiety is in a ratio of 1:1 to 1:20 regarding to the first or second antigen recognizing moiety.

The present invention reduces the incubation period for depletion of undesired cells to 5 minutes or less (see Example 5). In addition the sedimentation period can be reduced to 8 minutes or less resulting in an overall faster separation of target cells within about 15 minutes compared to methods known in the art (Example 5).

The present invention is strongly accelerated by the use of magnetic particles and applying a magnetic field gradient to them. The method works worse without the use of a magnetic field gradient resulting in additional sedimentation time needed and worse purity of cells compared to applying a magnetic field gradient (see Example 6).

The present invention works well in a large range of volume of the sample, e.g. it works with a 1.5 ml or 50 ml sample (see Example 7).

The present invention works well regardless if the cells to be separated are diluted with cell culture medium or in conventional buffer (see Example 8).

The present invention is reproducible and shows minor variation in performance between different samples (see Example 9). The method is also independent of the concentration of platelets (thrombocytes) available in the sample (see Example 10).

The erythrocyte aggregation reagent can be selected from the group consisting of dextran, hydroxyethyl starch, polyvinyl pyrrolidone (PVP), methylcellulose or hydroxypropylmethylcellulose (HPMC) as shown in Example 11. HPMC-15 is superior to other erythrocyte aggregation reagents as shown in Example 11. The optimal concentration of HPMC-15 used in the present invention is 0.2-0.5% HPMC15, e.g. in whole blood or buffycoat (Example 11).

In some embodiments of the present invention, the erythrocyte aggregation reagent is HPMC-15 and the mono-specific particle is a magnetic particle, preferentially between 100 and 1400 nm in size, more preferentially between 200 and 500 nm in size, coupled with e.g. anti CD61 monoclonal antibody. The anti CD61 antibody specifically binds to thrombocytes. The CD61 particle, the erythrocyte aggregation reagent and the whole blood sample are combined in a tube, containing e.g. a sample volume of 1.5 to 45 ml, and this mixture is incubated for 5 to 10 minutes and is gently mixed, e.g. on a rocker platform or manual mixture. Then the tube is stood upright in a rack and the magnetically labelled cells are separated in a magnetic field for 8-15 minutes. During this time the erythrocytes sediment to the bottom of the tube. In principle, cells can be recovered from the supernatant or from the cell pellet in which the pellet consists of the erythrocytes pellet at the bottom of the tube and the magnetically labelled cells retained at the sidewalls of the tube by the magnet. Normally, the desired cells are in the supernatant phase.

In some embodiments of the present invention, the erythrocyte aggregation reagent is HPMC-15 and the particles used are at least two mono-specific magnetic particles, preferentially between 100 and 1400 nm in size, more preferentially between 200 to 500 nm in size, coupled with e.g. anti CD61 monoclonal antibody and anti CD15 monoclonal antibody, respectively. The CD15 particle, the CD61 particle, and the erythrocyte aggregation reagent and the whole blood sample are combined in a tube, containing e.g. a sample volume of 1.5 to 45 ml, and this mixture is incubated for 5 to 10 minutes and is gently mixed, e.g. on a rocker platform or by manual mixture. Then the tube is stood upright in a rack and the magnetically labelled cells are separated in a magnetic field for 8-15 minutes. During this time the erythrocytes sediment to the bottom of the tube. Cells can be recovered from the supernatant.

In some embodiments of the present invention, the erythrocyte aggregation reagent is HPMC-15 and the particle used is a bi-specific magnetic particle, coupled with e.g. anti CD61 monoclonal antibody and anti CD15 monoclonal antibody in a ratio of 1:1. For achieving optimal results the ratio of coupling antibodies to the particle may vary and depends on the selected subsets of cells. The anti CD61 antibody specifically binds to thrombocytes and the anti CD15 antibody binds to granulocytes.

The CD61, CD15, particle, the erythrocyte aggregation reagent and the whole blood sample are combined in a tube, containing e.g. a sample volume of 1.5 to 45 ml, and this mixture is incubated for 5 to 10 minutes and is gently mixed, e.g. on a rocker platform or by manual mixture. Then the tube is stood upright in a rack and the magnetically labelled cells are separated in a magnetic field for 8-15 minutes. During this time the erythrocytes sediment to the bottom of the tube. Cells can be recovered from the supernatant.

In other embodiments of the present invention, the erythrocyte aggregation reagent is HPMC-15 and the particle used is a bi-specific magnetic particle, coupled with e.g. anti CD61 monoclonal antibody and anti CD15 monoclonal antibody in a ratio of 1:20. The CD61, CD15, bead, the erythrocyte aggregation reagent and the whole blood sample are combined in a tube and this mixture is incubated for 5 to 10 minutes and is gently mixed, e.g. on a rocker platform or by manual mixture. Then the tube is stood upright in a rack and the magnetically labelled cells are separated in a magnetic field for 8-15 minutes. During this time the erythrocytes sediment to the bottom of the tube. Cells can be recovered from the supernatant. The supernatant can be concentrated by e.g. filtration, either dead end filtration or cross flow/hollow fibre module filtration. For dead end filtration cells are given onto a filter with a pore size of e.g. 1 µm. Target cells are retained on the filter while liquid (i.e. serum diluted with buffer) drops through the filter. Target cells then are recovered from the filter surface by pipetting. For applications such as gene expression profiling the filter containing the target cells may be placed in a container with lysing solution for isolation of mRNA.

For cross flow filtration cells are placed in a syringe and passed through a module of hollow fibres into a second syringe. Some liquid (usually 10-30%) passes through the pores of the membranes into a third syringe. Cell suspension then is passed from the second to the first syringe and the process is repeated several times, gradually increasing cell concentration. When the desired volume is achieved, the syringes can be screwed of the hollow fibre module to recover the target cells.

In other embodiments of the present invention, the erythrocyte aggregation reagent is HPMC-15 and the particle used is a tri-specific magnetic particle, coupled with e.g. anti CD14 monoclonal antibody, anti CD36 monoclonal antibody and anti CD61 monoclonal antibody in a ratio of 2.5:2.5:1. The CD14, CD36, CD61, bead, the erythrocyte aggregation reagent and the whole blood sample are combined in a tube and this mixture is incubated for 5 to 10 minutes and is gently mixed, e.g. on a rocker platform or by manual mixture. Then the tube is stood upright in a rack and the magnetically labelled cells are separated in a magnetic field for 8-15 minutes. During this time the erythrocytes sediment to the bottom of the tube. Cells can be recovered from the supernatant.

In other embodiments of the present invention, the erythrocyte aggregation reagent is HPMC-15 and the bi-specific magnetic particle is a lyophilized magnetic particle, coupled with e.g. anti CD61 monoclonal antibody and anti CD15 monoclonal antibody. Before use the CD61.CD15.particles are solved within a liquid like $H_2O$ or any well suited buffer or cell culture medium. Then the CD61.CD15.particles, the erythrocyte aggregation reagent and the whole blood sample are combined in a tube and this mixture is incubated for 5 to 10 minutes and is gently mixed, e.g. on a rocker platform or by manual mixture. Then the tube is stood upright in a rack and the magnetically labelled cells are separated in a magnetic field for 8-15 minutes. During this time the erythrocytes sediment to the bottom of the tube. Cells can be recovered from the supernatant.

In other embodiments of the present invention, the erythrocyte aggregation reagent is HPMC-15 and the particle used is a bi-specific magnetic particle, coupled with e.g. anti CD61 monoclonal antibody and anti CD15 monoclonal antibody. The CD61, CD15, particle, the erythrocyte aggregation reagent and the whole blood sample are combined in a tube and this mixture is incubated for 5 to 10 minutes and is gently mixed, e.g. on a rocker platform or by manual mixture. Then the tube is stood upright in a rack and the magnetically labelled cells are separated in a magnetic field for 8-15 minutes. During this time the erythrocytes sediment to the bottom of the tube. Cells can be recovered from the supernatant. For a second round of separation of subsets of cells the supernatant directly or after washing or concentration of cells is used in methods suited for separation of cells normally used for PBMC or PBMC-like samples, e.g. Dynal-Beads or MicroBeads (Miltenyi Biotec GmbH, Germany). For example, enrichment of CD3+ cells is performed by using CD3+ MicroBeads. For another example enrichment of T cells is performed by using a T cell isolation kit.

In other embodiments of the present invention, the erythrocyte aggregation reagent is HPMC-15 and the particle used is a bi-specific magnetic particle, coupled with e.g. anti CD61 monoclonal antibody and anti CD15 monoclonal antibody. The CD61, CD15, particle, the erythrocyte aggregation reagent, a cell modification agent like e.g. the CD3 antibody, and the whole blood sample are combined in a tube and this mixture is incubated for 5 to 15 minutes and is gently mixed, e.g. on a rocker platform or by manual mixture. Then the tube is stood upright in a rack and the magnetically labelled cells are separated in a magnetic field for 8-15 minutes. During this time the erythrocytes sediment to the bottom of the tube. Cells can be recovered from the supernatant. For a second round of separation of subsets of cells the supernatant is applied directly or after concentration of cells for further cell separation to a MACS column. The target cells can be either the positive or negative selected cells.

In other embodiments of the present invention, the erythrocyte aggregation reagent is HPMC-15 and the particle is a mono- or multi-specific magnetic particle, coupled with monoclonal antibodies selected for an isolation kit (example 18-24). The antibody conjugated particles, the erythrocyte aggregation reagent and the whole blood sample are combined in a tube and this mixture is incubated for 5 to 15 minutes and is gently mixed, e.g. on a rocker platform or by manual mixture. Then the tube is stood upright in a rack and the magnetically labelled cells are separated in a magnetic field for 8-15 minutes. During this time the erythrocytes sediment to the bottom of the tube. Cells can be recovered from the supernatant. For a second round of separation antibody conjugated particles (e.g. CD235a and/or CD15 particles) are added to the supernatant, this mixture is incubated for 5 minutes, the tube is stood upright in a rack and the magnetically labelled cells are separated in a magnetic field for 5 minutes. Cells are recovered from the supernatant.

In some embodiments of the present invention, a cell separation composition comprises an erythrocyte aggregation reagent and a set of one or more mono- and/or multi-specific magnetic particles, with at least one antigen recognizing moiety coupled to the particles, wherein said particles with said at least one antigen recognizing moiety specifically bind to at least one antigen specific for one or more undesired cellular components.

In some embodiments of the present invention, a cell separation composition comprises an erythrocyte aggregation reagent and a set of one or more mono- and/or multi-specific magnetic particles with at least one antigen recognizing moiety coupled to the particles, wherein said particles with said at least one antigen recognizing moiety specifically bind to at least one antigen specific for one or more undesired cellular components, wherein said set comprises antigen specificities of the antigen recognizing moieties for granulocytes, e.g. CD15, and for platelets, e.g. CD61. This results in a cell composition in the supernatant of the present invention which is depleted of erythrocytes, thrombocytes and granulocytes (Example 18).

In other embodiments of the present invention, cell separation compositions comprise an erythrocyte aggregation reagent and a set of one or more mono- and/or multi-specific magnetic particles with at least one antigen recognizing moiety coupled to the particles, wherein said particles with said at least one antigen recognizing moiety specifically bind to at least one antigen specific for one or more undesired cellular components, and wherein said set comprises one or more, preferentially all, antigen specificities of the antigen recognizing moieties selected from the group consisting of CD2, CD14, CD15, CD36, CD43, CD56, CD61, aIgE. The use of all specificities results in a pure cell composition in the supernatant of the present invention of B cells (Example 19).

In other embodiments of the present invention, one or more, preferentially all, antigen specificities of the antigen recognizing moieties are selected from the group consisting of CD11b, CD14, CD15, CD19, CD36, CD56, CD61, CD123, aIgE. The use of all specificities results in a pure cell composition in the supernatant of the present invention of T cells (Example 20).

In other embodiments of the present invention, one or more, preferentially all, antigen specificities of the antigen recognizing moieties are selected from the group consisting of CD3, CD4, CD14, CD15, CD19, CD36, CD61, CD123, CD193, aIgE, aTCRab. The use of all specificities results in a pure cell composition in the supernatant of the present invention of NK cells (Example 21).

In other embodiments of the present invention, one or more, preferentially all, antigen specificities of the antigen recognizing moieties are selected from the group consisting of CD8, CD11b, CD14, CD15, CD19, CD36, CD56, CD61, CD123, aIgE, aTCRg/d. The use of all specificities results in a pure cell composition in the supernatant of the present invention of T helper cells (Example 23).

In other embodiments of the present invention, one or more, preferentially all, antigen specificities of the antigen recognizing moieties are selected from the group consisting of CD4, CD11b, CD14, CD15, CD19, CD36, CD56, CD61, CD123, aIgE, aTCRg/d. The use of all specificities results in a pure cell composition in the supernatant of the present invention of cytotoxic T cells (Example 24).

In other embodiments of the present invention, one or more, preferentially all, antigen specificities of the antigen recognizing moieties are selected from the group consisting of CD11b, CD14, CD15, CD19, CD36, CD56, CD61, CD123, aIgE, aTCRg/d. The use of all specificities results in a pure cell composition in the supernatant of the present invention of T cell receptor α/β positive T cells.

In other embodiments of the present invention, one or more, preferentially all, antigen specificities of the antigen recognizing moieties are selected from the group consisting of CD11b, CD14, CD15, CD19, CD36, CD56, CD61, CD123, aIgE, aTCRab. The use of all specificities results in a pure cell composition in the supernatant of the present invention of T cell receptor γ/δ positive T cells.

In other embodiments of the present invention, one or more, preferentially all, antigen specificities of the antigen recognizing moieties are selected from the group consisting of CD61, CD2, CD15, CD19, CD56, CD304, aIgE. The use of all specificities results in a pure cell composition in the supernatant of the present invention of monocytes (Example 22).

The cell separation components mentioned are suited to be provided as kit. Each kit contains the components necessary to perform the separation of desired cells from a blood cell-containing sample with the method described herein resulting in the cell compositions mentioned above.

Essential components are the erythrocyte aggregation reagents and the mono- or multi-specific particles as mentioned herein. The mono- and/or multi-specific particles may be available in the kit in liquids, e.g. buffers, or in a lyophilized form. Kits may be used for the isolation of B-cells, T-cells, T-helper cells, cytotoxic T-cells, natural killer cells, monocytes, neutrophils, eosinophils, basophils, hematopoietic stem cells, alpha/beta T cells and gamma/delta T cells.

The present invention in all its embodiments presented here may also be used for clinical applications. Exemplary the cells are isolated from leukapheresis harvests. Apheresis volume to be processed will typically be 150-250 mL, processed in a closed system such as a blood bag. Removal of the supernatant will be done e.g. by a plasma separator, either manual or automated. Target cells are either directly given to a patient (e.g. donor lymphocyte infusion) or manipulated (e.g. cultivated, stimulated and/or expanded or differentiated) before therapeutic application. Target cells can be derived from the patient (autologous use) or from a healthy donor (allogeneic use).

Target cell populations, such as T-cell populations, NK cell populations, monocytes of the present disclosure may be administered either alone, or as a pharmaceutical composition in combination with diluents and/or with other components such as IL-2, IL-7, IL-15 or other cytokines or cell populations. Briefly, pharmaceutical compositions of the present disclosure may comprise a target cell population as described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol; proteins; polypeptides or amino acids such as glycine; antioxidants; chelating agents such as EDTA or glutathione; adjuvants (e.g., aluminium hydroxide); and preservatives. A pharmaceutical composition may comprise a) a population of T cells, wherein said T cells are proliferated to therapeutically effective amounts according to standard procedures; and b) one or more pharmaceutically or physiologically acceptable carriers, diluents or excipients.

Another pharmaceutical composition may comprise a) a population of monocytes, wherein said monocytes are cultivated to generate dendritic cells according to standard procedures; and b) one or more pharmaceutically or physiologically acceptable carriers, diluents or excipients.

Another pharmaceutical composition may comprise a) a population of Natural Killer (NK) cells, wherein said NK cells are proliferated to therapeutically effective amounts according to standard procedures; and b) one or more pharmaceutically or physiologically acceptable carriers, diluents or excipients.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

EXAMPLES

Hereinafter, the present invention is described in more detail and specifically with reference to the examples, which however are not intended to limit the present invention.

Example 1: Size of Particles

Magnetic beads were manufactured with different process parameters according to Example 4, resulting in different size of the particles. Particle size was characterized by Beckman Coulter Delsa Nano instrument. Monoclonal antibodies recognizing CD15 and CD61 antigens were covalently conjugated to magnetic beads in a 1:1 ratio, resulting in 40 ug antibody per mL of bead suspension at a concentration of OD450=10.

Different amounts of conjugated beads and 0.2 mL of a 2% stock solution of hydroxypropylmethylcellulose were given to 1 mL of Buffy Coat from human whole blood within a 5 mL FACS tube, mixed for 15 minutes within MACSmix™ Tube rotator (Miltenyi Biotec) and placed in a MACSiMag™ Separator for 20 minutes. Supernatant was completely removed using a pipette, transferred to a FACS Tube, cells were counted using a Sysmex KX21 hematology analyzer and cells were analyzed using a MACSquant Analyzer flow cytometer (Miltenyi Biotec).

Erythrocytes, thrombocytes and granulocytes were removed from whole blood with >99% efficiency when conjugated particles with a diameter of 214 um, 250 um, 290 um were used. Thrombocyte and granulocyte removal was less efficient, when 1400 um particles were used. (see FIG. 1 to FIG. 4)

Example 2: Mono-Specific Particles

Figure 5:
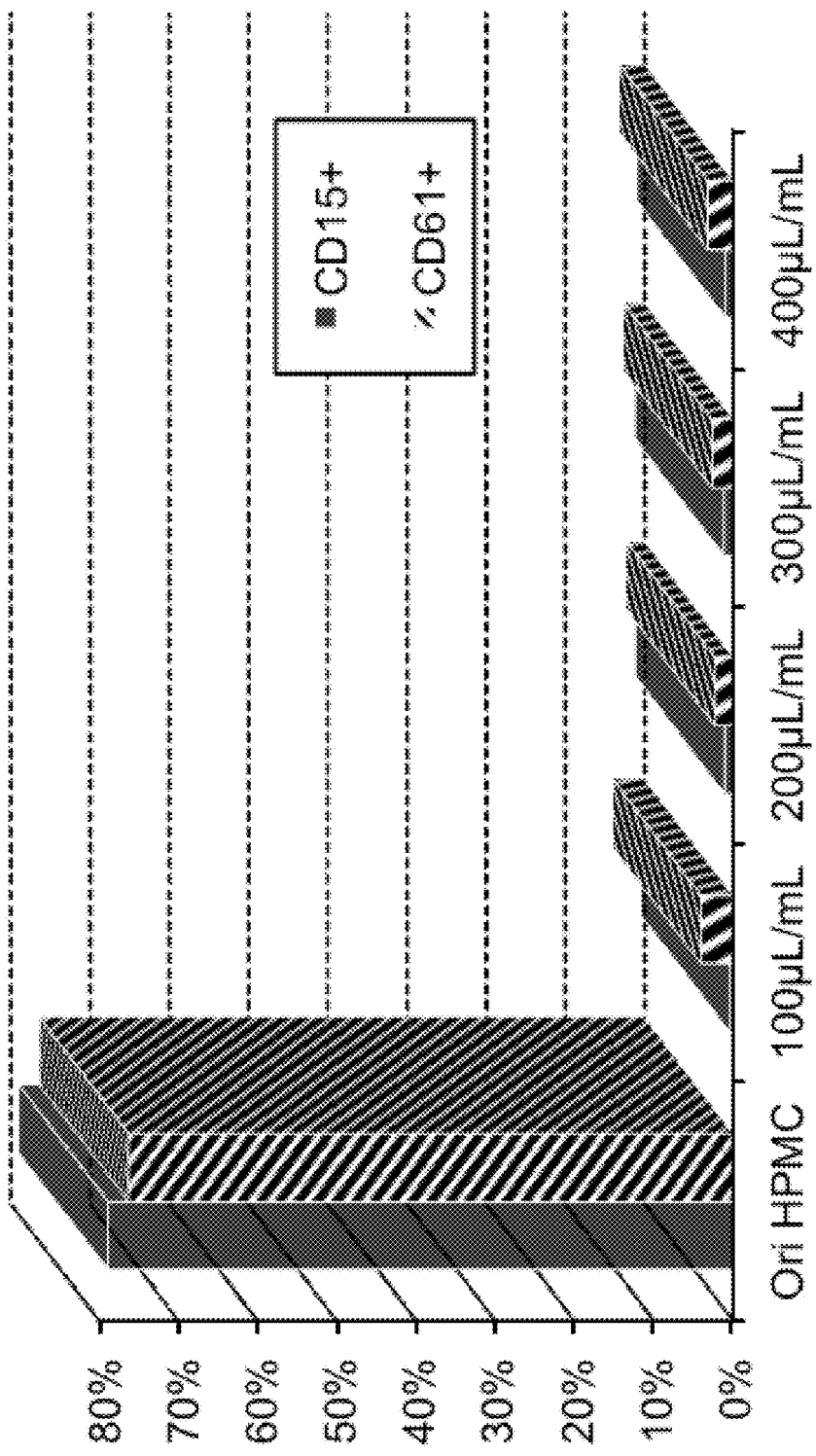
FIG. 5: Granulocyte and thrombocyte depletion efficiency of conjugates of 100 nm magnetic beads conjugated to CD15 and CD61 antibodies

Monoclonal antibodies recognizing CD15 and CD61 were individually conjugated to magnetic beads (Example 4, average diameter 100 nm). Bead conjugated antibodies were given to 1.3 mL of whole blood, 0.7 mL of PBS buffer and 200 ul of HPMC15 stock solution. Granulocytes and platelets, respectively or combined, were removed for 98% to >99%, (see FIG. 5).

Monoclonal antibodies recognizing CD19 and CD56 were individually conjugated to magnetic beads (Example 4, average diameter 220 um). Bead conjugated antibodies were given to 1.3 mL of whole blood, 0.7 mL of PBS buffer and 200 ul of HPMC15 stock solution. B cells and NK cells respectively were removed for >98% (see FIG. 6 and FIG. 7).

Example 3: Multi-Specific Particles

Either 2, 3, 4, 6 or 8 different antibodies were conjugated to either 100 nm or 200 nm magnetic beads (see Example 4) in previously evaluated antibody ratios. Antibody ratios were determined by titrating mono-specific conjugates and determining individually the lowest amount of antibody sufficient for complete removal of a cell subset. The individual antibody concentrations were used to calculate ratios. Bead conjugated antibodies were given to 1.3 mL of whole blood, 0.7 mL of PBS buffer and 200 ul of 2% HPMC15 stock solution, mixed for 15 minutes within MACSmix™ Tube rotator (Miltenyi Biotec) and placed in a MACSiMag™ Separator for 20 minutes. Supernatant was completely removed using a pipette, transferred to a FACS Tube, cells were counted using a Sysmex KX21 hematology analyzer and cells were analyzed using a MACSquant Analyzer flow cytometer (Miltenyi Biotec). More than 92% of the cell populations analyzed were depleted, see FIG. 8.

Example 4: Generation of Particles

The generation of superparamagnetic particles as used herein is disclosed in U.S. Pat. No. 5,543,289 which is included herewith by reference. The range of size of beads achieved can be influenced by the dextran concentration used during precipitation of the beads and by the iron salts used.

Other beads were commercial available: 250 nm Kisker-Beads were purchased from Kisker Biotech (Germany), micrometer sized particles were from SensScreen Technologies (Germany) or Miltenyi Biotec (MACSiBeads).

FIG. 9 shows the size distribution of a magnetic particle conjugated to a CD56 antibody generated by the modified method of U.S. Pat. No. 5,543,289. The size of a conjugate of magnetic particles conjugated to a CD56 antibody has been determined by measurement on a Beckman Coulter Delsa Nano instrument. Average diameter is 260 nm. About 95% of beads are within the range of 100 nm to 1400 nm in diameter, about 90% of beads are within the range of 200 nm to 500 nm in diameter Example 5: Incubation and Sedimentation Periods The present invention was used according to protocols described in Examples 1, 2 and 3 using an CD4/CD61 magnetic bead conjugate (200 nm diameter).

Incubation times of 0, 5, 10 and 15 minutes were compared. Sedimentation time was always 20 minutes. An incubation time of 5 minutes resulted in comparable depletion to that obtained with 15 minutes incubation time.

In a second experiment sedimentation times of 8, 10, 12, 15 and 20 minutes were compared after 5 minutes incubation time. A sedimentation time of 8 minutes resulted in comparable depletion to that obtained with 20 minutes sedimentation time. Further reduced sedimentation time was not evaluated as the erythrocyte had not been fully sedimented with sedimentation time of less than 8 minutes.

Example 6: Separation By Gravitational Force

Cocktails of antibody conjugated magnetic beads (200 nm size, see Examples 19 and 21) were used according to protocols described in examples 1, 2 and 3 to compare sedimentation by gravity sedimentation and by magnetically enforced sedimentation.

NK cells were enriched from 6.4% in whole blood to 8.1% and 70.2% respectively. B cells were enriched from 4.5% to 23.4% and 85.5% respectively.

Thus enrichment of target cells is general possible by non-magnetically enforced sedimentation but clearly worse than if magnetically enforced sedimentation is applied. Purity of target cells is significantly improved, if sedimentation is magnetically enforced.

Example 7: Separation of Different Volume of the Sample

Different scales of cell separation were compared using protocols similar to Examples 1, 2 and 3. Buffy Coat from human whole blood was used, scale of separation was 2 mL vs 13.5 mL vs. 45 mL using 1.3 mL/9 mL/30 mL of buffy coat diluted with half the volume of Phosphate Buffered Saline solution. Antibody conjugates used were CD61 and CD15 antibodies bi-specifically conjugated to 100 nm and 200 nm magnetic beads.

Removal of erythrocytes, platelets and granulocytes was equivalent in all three scales. Removal was >99% for erythrocytes, >99% for platelets and >95% for granulocytes.

Example 8: Separation With Medium Instead of Buffer

Separation has been performed with RPMI 1640 cell culture medium instead of PBS buffer for dilution steps, resulting in a cell suspension in 67% autologous serum and 33% cell culture medium, a configuration that can directly be used for cell culture assay. Separation was evaluated in 2 mL scale in 5 mL FACS tubes, using human whole blood, 200 uL of HPMC15 stock solution and 200 nm magnetic beads conjugated to a cocktail of antibodies directed against CD3, CD4, CD14, CD15, CD19, CD36, CD61, CD123 antibodies. Purity and yield of isolated NK cells were equivalent using both RPMI 1640 cell culture medium and PBS buffer supplemented with 0.5% bovine serum albumin.

Example 9: Variation of Performance Induced By Different Patient Samples

NK cells were isolated from 10 donors using the current invention and separation performance was compared to a commercially available whole blood NK cell isolation kit (Rosette Sep NK cell isolation kit, Stem Cell Technologies).

The current invention was evaluated using a cocktail of bi-specific antibody magnetic bead conjugates (200 nm diameter) consisting of CD61, CD3 Beads, CD61, CD14 Beads, CD61, CD15 Beads, CD61, CD19 Beads, CD61, CD4 Beads, all of them with an antibody ratio of 1:19. 200 ul of a 2% HPMC15 stock solution was used. Reagents were incubated for 15 minutes, magnetically enforced sedimentation was performed for 20 minutes using a MACSiMAG™ separator (Miltenyi Biotec). Purity of isolated NK cells among lymphocytes was 76.1%±10.2% compared to 74.1%±11% using the Rosette Sep system. Yield of NK cells was 66±11% (present invention) vs. 44±19%.

Purity and yield of NK cells are equivalent to or superior to commercially available products, variability of yield is significant lower.

Example 10: Independence of Concentration of Platelets

In the present invention parallel depletion of erythrocytes, platelets and non desired cells, i.e. non-target leukocytes, is performed. It has been evaluated whether low or high platelet content in whole blood impacts separation performance and purity of target cells. Blood samples have been centrifuged at 200 g for 10 minutes, pelleting the erythrocytes and leukocytes and leaving most of the platelets in the supernatant. Supernatant of blood samples has either been removed or added to other samples to reduce or increase the platelet concentration. Cell separation has been performed according to protocols described in Examples 1, 2 and 3. Purity and yield of target cells (NK cells) were identical. Thus platelet concentration of the sample to be processed does not affect separation performance of the present invention.

Example 11: Erythrocyte Aggregation Reagent

Different amounts and concentrations of the erythrocyte sedimentation reagent HPMC-15 have been evaluated as components of an NK cell selection procedure: 100, 200, 300, 400, 500, 600 ul of a 2% HPMC15 stock solution have been used per mL of either human whole blood or buffy in a 2 mL scale. Higher concentration of HPMC15 reduced yield of target cells (NK cells) and increased purity of NK cells. The optimum amount of 2% HPMC15 stock solution was 200-250 ul/mL of whole blood or buffy coat, resulting in a final concentration of about 0.2% HPMC15.

Figure 19:
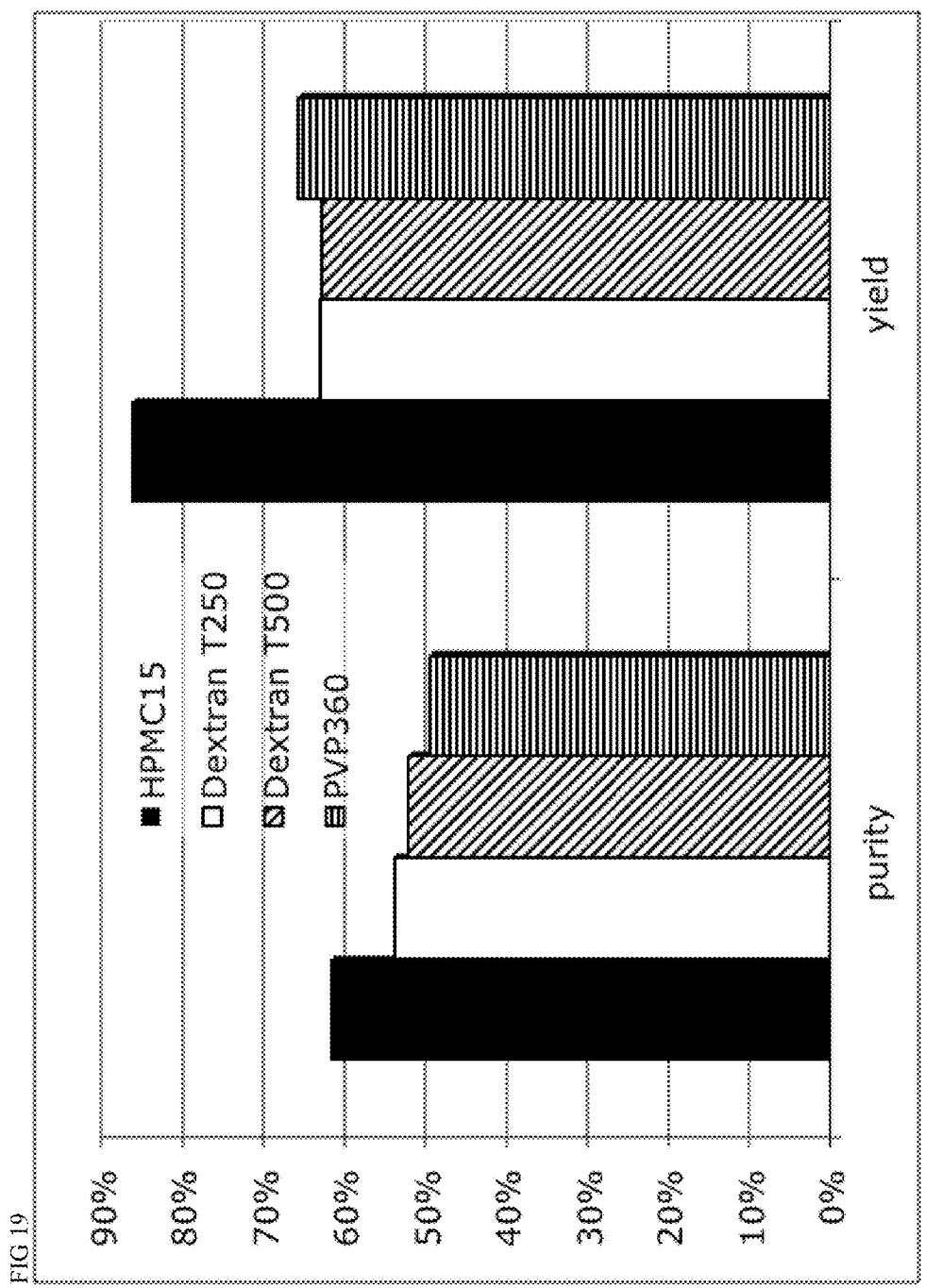
FIG. 19: Purity and yield of NK cells isolated in combination of a an antibody cocktail conjugated to magnetic particles and different erythrocyte aggregation reagents

HPMC15 was compared to other erythrocyte sedimentation reagents, namely Dextran T250, Dextran T500, PVP 360 using a cocktail of CD3, CD4, CD14, CD15, CD19, CD36, CD61 and CD123 antibodies conjugated to 200 nm magnetic beads. All combinations resulted in enrichment of NK cells, HPMC15 resulted in the highest purity and yield of NK cells (61.8% purity and 86% yield vs 53.8%, 52.0%, 49.4% purity and 63%, 63%, 66% yield for Dextran T250, Dextran T500 and PVP respectively; FIG. 19)

Erythrocyte aggregation reagents were also compared when not combined with antibody conjugated magnetic particles. Platelet content was reduced by 76% using HPMC-15, by only 8% using Dextran T250, by only 13% using Dextran T500 and by only 47% using PVP. The high platelet removal efficiency of HPMC-15 can synergistically be combined with platelet bindig antibody (such as CD61) conjugated to magnetic particles.

Example 12: Particles Coupled Indirectly With Antibodies

Magnetic Beads (<100 nm diameter) conjugated to antibodies recognizing constant regions of a secondary antibody or fluorochromes of antibody conjugates have been loaded with secondary antibodies/antibody conjugates recognizing CD3 and CD19 antigens. T and B cells, respectively, have been depleted by 91.5% and 99.1% using CD3-PE and CD19-PE, by 94% and 99.9% using CD3-APC and CD19-APC, by 95.3% and 98.6% using CD3-FITC and CD19-FITC, by 94.1% and 99.4% using CD3 and CD19 antibodies (and anti-IgG magnetic beads), by 88% and 98.6% using CD3-Biotin and CD19-Biotin respectively.

All indirect separation systems showed equivalent separation performances compared to the use of antibodies that were directly conjugated to magnetic beads.

Example 13: Use of Different Samples

The present invention has been evaluated on different erythrocyte containing cell products, namely leukapheresis harvest, cord blood, bone marrow aspirates using CD15 and CD61 antibodies conjugated to 200 nm magnetic beads. In all cases >99% of granulocytes and >96% of platelets were removed.

The current invention has been evaluated on bone marrow aspirates using CD19 and CD56 antibodies conjugated to 200 nm magnetic beads. 99% of B cells and 87% of NK cells were removed.

The present invention has been evaluated on buffy coat preparations from whole blood using CD61 and CD15 antibodies conjugated to 100 nm magnetic beads and CD61 and CD19 antibodies conjugated to 100 nm magnetic beads. 99.7% of platelets and 97% of granuloctes and 99.4% of platelets and 97% of B cells were removed.

The present invention thus can successfully be used for samples such as whole blood, buffy coat preparations, leukapheresis harvests, cord blood and bone marrow aspirates, but is not limited to these samples. The present invention will work with any sample which contains erythrocytes and other cellular components. Such samples may also be artificially generated, e.g. by adding erythrocytes to a sample which originally contains no erythrocytes, e.g. cell culture.

Example 14: Rosette Sep Principle Without Centrifugation

In order to evaluate whether current technology is feasible for cell separation directly from whole blood without centrifugation steps a erythrocyte rosetting method (RosetteSep, Stem Cell Technologies) has been evaluated according to Examples provided in U.S. Pat. No. 6,872,567 B2 using Dextran or HPMC15 as erythrocyte aggregation reagents. The RosetteSep Monocyte Isolation Cocktail has been incubated with 5 mL of Buffy Coat from human whole blood and either Dextran T 500 or HPMC15 for 10 minutes. Red blood cells did not sediment although they did in control experiments without the antibody cocktail.

Cell suspension was centrifuged at 50×g for 5 minutes. Supernatant was recovered and analyzed by flow cytometry. Monocytes were enriched from 8.92% to 37.9% (Dextran) and 35.2% (HPMC) respectively at a yield of 28.3%/11.5%, compared to reference values provided by the supplier of 71±9% purity and 57±23% yield, when using the Kit with a Ficoll procedure.

The combination of erythrocyte sedimentation and non-target cell rosetting with erythrocytes did not work at all without centrifugation and did not provide sufficient separation performance after centrifugation.

Example 15: Whole Blood Separation Method With and Without CD235a Antibodies

A cocktail of antibodies (see Example 3, specificities see Example 21) has been conjugated to magnetic particles (>200 nm) and used according to protocols provided in Examples 1, 2 and 3 and separation performance has been compared to an experiment where an CD235a (GlycophorinA) antibody has been conjugated to the same kind of magnetic particles and used either in a second step to further reduce erythrocyte content or combined with the conjugated antibody cocktail. Purity of isolated NK cells was not significantly improved by addition of the CD235a conjugate (94.2% vs. 92.8). Erythrocyte content in the final cell preparation was only reduced by 44% (4.6E+06 RBC vs. 8.2E+06, i.e. 0.073% vs 0.130% of initial number). In contrast, erythrocyte content could be reduced below the detection limit by depleting CD235a positive erythrocytes in a second step. I.e. addition of CD235a conjugated beads is not necessary to obtain high purities and not sufficient to completely remove erythrocytes. Complete removal of erythrocytes can be achieved by using CD235a magnetic beads in a second separation step.

Example 16: Lyophilized Reagent vs. Liquid Reagent

An NK cell isolation kit has been configured based on the present invention (see Example 21). Reagents have either been stored at 4° C., at −70° C. after freezing or have been lyophilized with supplements and procedures as known in the art. Lyophilized reagents have been reconstituted with 0.75× Phosphate buffered saline. Compositions have been used for NK cell isolation according to the present invention.

Figure 10:
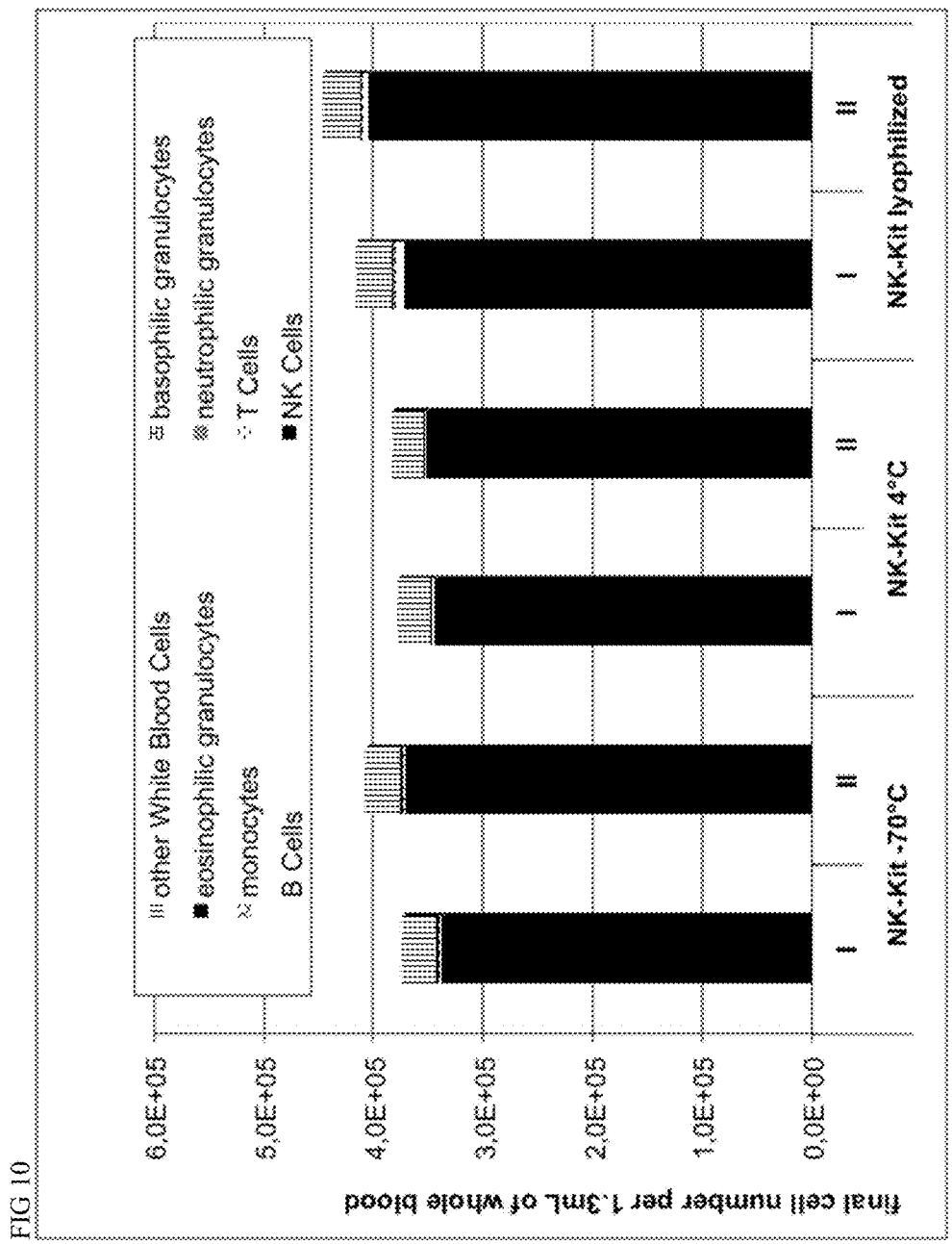
FIG. 10: Separation efficiency of an NK cell kit containing 220 nm magnetic beads conjugated to non-NK cell antibodies and HPMCafter storage in liquid and lyphilized format

NK cells were purified to 90%, 92%, 90% purity respectively with a yield of 72%, 71%, 83% respectively. (see FIG. 10)

Example 17: Lyophilized Reagent Reconstituted With Different Buffers

An NK cell isolation kit has been configured based on the present invention (see Example 21). Reagents have been lyophilized with supplements and procedures as known in the art.

Lyophilized reagents have been reconstituted with 0.75× Phosphate with different supplements:
  0.3125% BSA/0.75% HPMC
  0.3125% BSA/0.75% HPMC/0.03% Pluronic/0.05% NaAzid
  0.75% HPMC/0.03% Pluronic/0.05% NaAzid
  0.75% HPMC/0.03% Pluronic
  0.75% HPMC/buffered saline.

Figure 11:
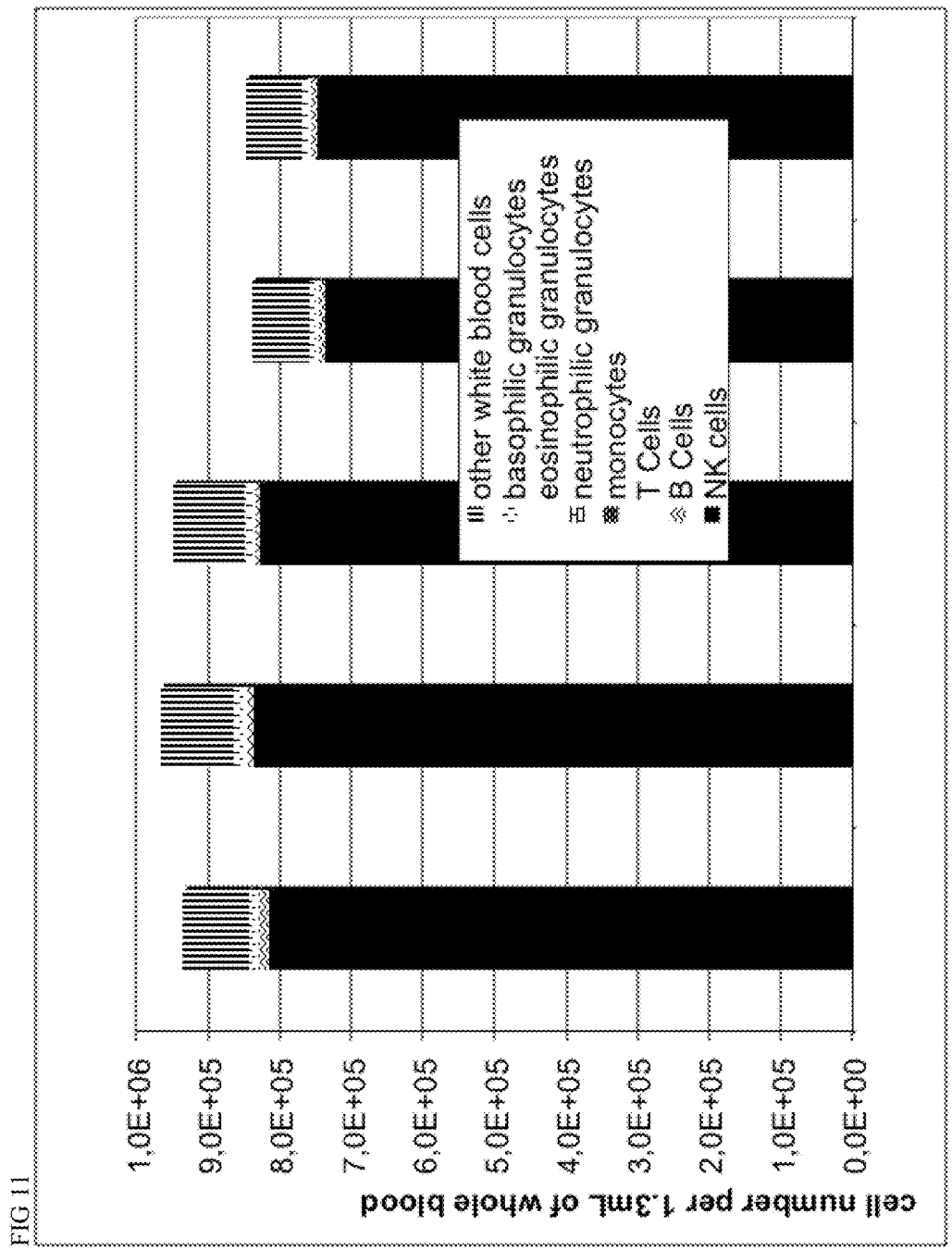
FIG. 11: Separation efficiency of an lyophilized NK cell kit containing 220 nm magnetic beads conjugated to non-NK cell antibodies and HPMC reconstituted with different buffers

Compositions have been used for NK cell isolation according to the present invention. NK cells were purified to 87-88% purity with a yield of 63-71% (see FIG. 11).

Example 18: Peripheral Blood Mononuclear Cell Kit Combination

Magnetic particles (Example 4) have been conjugated to antibodies recognizing CD15 and CD61. Antibody bead conjugates have been titrated on human whole blood and the optimal concentration has been determined. Magnetic bead antibody conjugates have been combined to a cocktail at the previously determined amounts.

The antibody cocktail has been given to 1.5 mL of human whole blood, mixed, incubated for 5 minutes in a MACSmix™ Tube rotator (Miltenyi Biotec GmbH) and placed in a magnet (FIG. 17) for 8 minutes. Supernatant has been recovered by pipetting into a new tube. Isolated peripheral blood mononuclear cells have been analyzed on a MACSquant Analyzer flow cytometer (Miltenyi Biotec) using a combination of fluorochrome-conjugated antibodies.

Example 19: B Cell Kit Combination

Magnetic particles (Example 4) have been conjugated to antibodies recognizing CD2, CD14, CD15, CD36, CD43, CD56, CD61 and aIgE. Antibody bead conjugates have been titrated on human whole blood and the optimal concentration has been determined. Magnetic bead antibody conjugates have combined to a cocktail at the previously determined amounts. The antibody cocktail has been given to 1.5 mL of human whole blood, mixed, incubated for 5 minutes in a MACSmix™ Tube rotator (Miltenyi Biotec GmbH) and placed in a magnet (FIG. 17) for 8 minutes. Supernatant has been recovered by pipetting into a new tube. Isolated B cells have been analyzed on a MACSquant Analyzer flow cytometer (Miltenyi Biotec) using a combination of fluorochrome-conjugated antibodies.

Example 20: T Cell Kit Combination

Magnetic particles (Example 4) have been conjugated to antibodies recognizing CD11b, CD14, CD15, CD19, CD36, CD56, CD61, CD123, aIgE. Antibody bead conjugates have been titrated on human whole blood and the optimal concentration has been determined. Magnetic bead antibody conjugates have combined to a cocktail at the previously determined amounts.

The antibody cocktail has been given to 1.5 mL of human whole blood, mixed, incubated for 5 minutes in a MACSmix™ Tube rotator (Miltenyi Biotec GmbH) and placed in a magnet (FIG. 17 for 8 minutes. Supernatant has been recovered by pipetting into a new tube. Isolated T cells have been analyzed on a MACSquant Analyzer flow cytometer (Miltenyi Biotec) using a combination of fluorochrome-conjugated antibodies.

Example 21: NK Cell Kit Combination

Magnetic particles (Example 4) have been conjugated to antibodies recognizing CD3, CD4, CD14, CD15, CD19, CD36, CD61, CD123, CD193, aIgE, aTCRab. Antibody bead conjugates have been titrated on human whole blood and the optimal concentration has been determined. Magnetic bead antibody conjugates have combined to a cocktail at the previously determined amounts.

The antibody cocktail has been given to 1.5 mL of human whole blood, mixed, incubated for 5 minutes in a MACSmix™ Tube rotator (Miltenyi Biotec GmbH) and placed in a magnet (FIG. 17) for 8 minutes. Supernatant has been recovered by pipetting into a new tube. Isolated NK cells have been analyzed on a MACSquant Analyzer flow cytometer (Miltenyi Biotec) using a combination of fluorochrome-conjugated antibodies.

Example 22: Monocyte Kit Combination

Magnetic particles (Example 4) have been conjugated to antibodies recognizing CD3, CD7, CD15, CD19, CD56, CD61, CD123, CD193, CD304, CD335, aIgE. Antibody bead conjugates have been titrated on human whole blood and the optimal concentration has been determined. Magnetic bead antibody conjugates have combined to a cocktail at the previously determined amounts.

The antibody cocktail has been given to 1.5 mL of human whole blood, mixed, incubated for 5 minutes in a MACSmix™ Tube rotator (Miltenyi Biotec GmbH) and placed in a magnet (FIG. 17) for 8 minutes. Supernatant has been recovered by pipetting into a new tube. Isolated monocytes have been analyzed on a MACSquant Analyzer flow cytometer (Miltenyi Biotec) using a combination of fluorochrome-conjugated antibodies.

Example 23: T Helper Cell Kit Combination

Magnetic particles (Example 4) have been conjugated to antibodies recognizing CD8, CD11b, CD14, CD15, CD19, CD36, CD56, CD61, CD123, aIgE, aTCRg/d. Antibody bead conjugates have been titrated on human whole blood and the optimal concentration has been determined. Magnetic bead antibody conjugates have combined to a cocktail at the previously determined amounts.

The antibody cocktail has been given to 1.5 mL of human whole blood, mixed, incubated for 5 minutes in a MACSmix™ Tube rotator (Miltenyi Biotec GmbH) and placed in a magnet (FIG. 17) for 8 minutes. Supernatant has been recovered by pipetting into a new tube. Isolated helper T cells have been analyzed on a MACSquant Analyzer flow cytometer (Miltenyi Biotec) using a combination of fluorochrome-conjugated antibodies.

Example 24: Cytotoxic T Cell Kit Combination

Magnetic particles (Example 4) have been conjugated to antibodies recognizing CD4, CD11b, CD14, CD15, CD19, CD36, CD56, CD61, CD123, aIgE, aTCRg/d. Antibody bead conjugates have been titrated on human whole blood and the optimal concentration has been determined. Magnetic bead antibody conjugates have combined to a cocktail at the previously determined amounts.

The antibody cocktail has been given to 1.5 mL of human whole blood, mixed, incubated for 5 minutes in a MACSmix™ Tube rotator (Miltenyi Biotec GmbH) and placed in a magnet (FIG. 17) for 8 minutes. Supernatant has been recovered by pipetting into a new tube. Isolated cytotoxic T cells have been analyzed on a MACSquant Analyzer flow cytometer (Miltenyi Biotec) using a combination of fluorochrome-conjugated antibodies.

Example 25: Two Parameter Sort

Peripheral blood mononuclear cells have been isolated from 20 ml of human whole blood using the disclosed invention according to Example 18. Isolated peripheral blood mononuclear cells have been washed by a 300×g centrifugation step and applied to an equilibrated MACS LS column (Miltenyi Biotec). Flow through has been collected, cells have been counted and 1E7 white blood cells have been magnetically labelled in 100 ul using CD19 Microbeads according to the manufacturer's instruction (Miltenyi Biotec GmbH). B cells have been purified to 81.2% purity with a yield of 79.8% using a MACS MS column. For comparison peripheral blood mononuclear cells have been isolated using the present invention according to example 18. 1E7 isolated peripheral blood mononuclear cells have been magnetically labelled in 100 ul using a MACS B cell isolation kit. B cells have been purified to 89.7% with a yield of 95%.

Example 26: Sedimentation Speed

Sedimentation speed of human whole blood supplemented with either erythrocyte aggregation solution (HPMC-15) or erythrocyte aggregation solution and magnetic beads of different size (50 nm, 200 nm, 3500 nm) conjugated to a cocktail of monoclonal antibodies (CD3, CD14, CD15, CD19, CD36, CD61, CD123, anti IgE) has been evaluated by determining the volume of the supernatant that can be removed. Surprisingly the combination of HPMC-15 and 200 nm sized antibody conjugated magnetic beads resulted in complete sedimentation of erythrocytes within 3 minutes compared to 8.5 minutes when only the erythrocyte aggregation solution (HPMC) was used). Sedimentation was slower when smaller or larger magnetic beads were used. FIG. 18 shows results of the experiment.

Example 27: Use of CD36 Conjugated Magnetic Beads 2.5 mL of whole blood have been used for isolation of CD8 positive cytotoxic lymphocytes by the present invention, using HPMC-15 and a cocktail of monospecific magnetic particles (220 nm) conjugated to CD4, CD11b, CD14, CD15, CD19, CD56, CD61, CD123, aIgE, aTCRg/d antibodies. CD36 antibody conjugated beads have either been added to the cocktail or cocktail has been used without addition of CD36 antibody. 2.4 mL of supernatant could be recovered with the approach without CD36 antibody conjugated particles, containing 73% of the initial amount of CD8 positive cells at a purity of 80.4%. The pellet shape was as depicted in FIG. 13, providing a flat interface between sedimented pellet and supernatant phase. When CD36 antibody conjugates magnetic particles were used the exponential shape of the sedimented pellet (FIG. 14) allowed for a larger volume of supernatant (2.6 ml; +8%) to be recovered, increasing yield to 78% at a purity of 80.7%.

Example 28: Comparing Magnet Designs 8 mL of buffy coat from whole blood have been depleted of erythrocytes, platelets and granulocytes using the present invention (CD61 and CD15 antibodies conjugated to 200 nm magnetic particles in a 1:1 ratio, HPMC-15 containing buffer for dilution with 4 mL) combined with different magnets. The MACSiMAG separator depleted 99.1% of granulocytes and 99.2% of platelets, the magnetic aquarium glass cleaner 97.6% and 98.7% respectively, a design with 3 magnets in a U shaped yoke 99.7% and 98.0% respectively, the SensScreen magnet 96.7% and 98.6% respectively.

The magnet according to FIG. 17 was compared to the MACSiMAG separator using 1 mL of whole blood, HPMC-15 containing PBS buffer, an NK cell isolation kit consisting of non-NK cell binding antibodies conjugated to 240 nm magnetic particles. Blood was incubated with the reagents for 5 minutes, sedimentation time was 8 minutes. NK cells were purified to 81% purity at 67% yield using the magnet according to FIG. 17 and to 77.6% purity at 66% yield using the MACSiMAG separator.

Example 29: B Cell Depletion Using 50 nm Magnetic Particles

A monoclonal antibody recognizing CD19 on B cells was conjugated to magnetic beads (Example 4, average diameter 50 nm, MicroBeads, Miltenyi Biotec). Bead conjugated antibody was given to 1.3 mL of buffy coat from whole blood, 0.7 mL of PBS buffer and 200 ul of HPMC15 stock solution. B cells were only unsufficiently depleted with more than 75% of B cells remaining in the sample (see FIG. 12).

The invention claimed is:
1. A depletion method for purifying a target leukocyte subpopulation from a starting sample containing erythrocytes and other types of leukocytes, the method comprising:
    combining the starting sample with a cocktail of reagents to form a separation mixture, wherein the cocktail comprises as separate components:
        (1) a plurality of different antigen-recognizing moieties specific for cell markers on the other types of leukocytes but not on the target leukocytes, attached directly or indirectly to magnetic particles; and
        (2) a preselected choice and concentration of an erythrocyte aggregation reagent;
    performing a single separation step of magnetically enforced sedimentation by placing the separation mixture in a magnetic field such that the erythrocytes and the other types of leukocytes form a pellet, leaving a supernatant phase; and
    harvesting the target leukocyte subpopulation from the supernatant phase;
    wherein the size of the magnetic particles, the concentration of the magnetic particles, the choice of the erythrocyte aggregation reagent, and the concentration of the erythrocyte aggregation reagent in the cocktail of reagents are all preselected such that the single separation step produces a population of the target leukocytes in the supernatant phase from a sample of whole blood that is over 60% pure and constitutes a yield of over 40% of the number of target leukocytes in said sample.

2. The depletion method of claim 1, wherein the cocktail of reagents further comprises antigen-recognizing moieties that are specific for erythrocytes attached directly or indirectly to magnetic particles.

3. The depletion method of claim 1, with the proviso that the erythrocyte aggregation agent is not dextran.

4. The depletion method of claim 1, with the proviso that the cocktail of reagents does not include antigen-recognizing moieties specific for CD235a (glycophorin A).

5. The method of claim 1, wherein the starting sample is a sample of whole blood.

6. The method of claim 1, wherein the starting sample is a leukopheresis sample, a buffy coat sample, an umbilical cord sample, or a bone marrow sample.

7. The depletion method of claim 1, wherein the single separation step produces a population of the target leukocytes in the supernatant phase from the starting sample that is at least 76% pure.

8. The depletion method of claim 1, wherein the single separation step produces a population of the target leukocytes in the supernatant phase from the starting sample that is at least 90% pure.

9. The depletion method of claim 1, wherein the single separation step produces a population of the target leukocytes in the supernatant phase that has a yield of at least 66% of the target leukocyte subpopulation in the starting sample.

10. The depletion method of claim 1, wherein the single separation step produces a population of the target leukocytes in the supernatant phase that has a yield of at least 83% of the target leukocyte subpopulation in the starting sample.

11. The depletion method of claim 1, wherein the single separation step produces a supernatant phase from which over 99% of the erythrocytes in the sample have been depleted.

12. The method of claim 1, wherein the pellet is separated into two parts: one part at the bottom of a container in which the mixture is subject to the magnetically enforced sedimentation, the other part along a vertical side of the container.

13. The method of claim 1, wherein the erythrocytes and the other types of leukocytes from the starting sample form a combined pellet having a curved surface.

14. The method of claim 1, further comprising removing residual erythrocytes from the cell population recovered from the supernatant phase using an antigen recognizing moiety specific for an erythrocyte specific marker.

15. The method of claim 1, wherein the target leukocyte subpopulation is a purified population of NK cells, B lymphocytes, T lymphocytes, monocytes, T helper cells, or cytotoxic T cells.

16. The method of claim 15, wherein the target leukocyte subpopulation is a purified population of NK cells, and the cocktail of reagents contains antigen-recognizing moieties specific for CD3, CD4, CD14, CD15, CD19, CD36, CD61, CD123, CD193, IgE, and T cell receptor (TCR).

17. The method of claim 15, wherein the target leukocyte subpopulation is a purified population of B lymphocytes, and the cocktail of reagents contains antigen-recognizing moieties specific for CD2, CD14, CD15, CD36, CD43, CD56, CD61, and IgE.

18. The method of claim 15, wherein the target leukocyte subpopulation is a purified population of T lymphocytes, and the cocktail of reagents contains antigen-recognizing moieties specific for CD11b, CD145, CD15, CD19, CD36, CD56, CD61, CD123, and IgE.

19. The method of claim 15, wherein the target leukocyte subpopulation is a purified population of monocytes, and the cocktail of reagents contains antigen-recognizing moieties specific for CD3, CD7, CD15, CD19, CD56, CD61, CD123, CD193, CD304, CD335, and IgE.

20. The method of claim 1, further comprising formulating the leukocytes harvested from the supernatant phase as a pharmaceutical composition by way of a process that includes combining the harvested leukocytes with a pharmaceutical carrier or excipient.

21. A depletion method for purifying a target leukocyte subpopulation from a starting sample containing erythrocytes, thrombocytes, and other types of leukocytes, the method comprising:
  combining the starting sample with a cocktail of reagents to form a separation mixture, wherein the cocktail comprises as separate components:
    (1) a plurality of different antigen-recognizing moieties specific for cell markers on the other types of leukocytes but not on the target leukocytes, attached directly or indirectly to magnetic particles;
    (2) antigen-recognizing moieties specific for platelets, attached directly or indirectly to magnetic particles; and
    (3) an erythrocyte aggregation reagent;
  performing a single separation step of magnetically enforced sedimentation by placing the separation mixture in a magnetic field such that the erythrocytes, the platelets, and the undesired leukocytes form a pellet, leaving a supernatant phase from which over 90% of the platelets in the starting sample have been depleted; and
  harvesting the target leukocytes from the supernatant phase.

22. The depletion method of claim 21, wherein the antigen-recognizing moieties specific for platelets include moieties specific for CD61, CD62, and/or CD41.

23. The depletion method of claim 21, wherein the single separation step produces a supernatant phase from which over 97% of the platelets in the sample have been depleted.

24. A depletion method for purifying a target leukocyte subpopulation from a starting sample containing erythrocytes, granulocytes, and other types of leukocytes, the method comprising:
  combining the starting sample with a cocktail of reagents to form a separation mixture, wherein the cocktail comprises as separate components:
    (1) antigen-recognizing moieties specific for granulocytes, attached directly or indirectly to magnetic particles;
    (2) a plurality of different antigen-recognizing moieties specific for cell markers on other types of leukocytes but not on the target leukocytes, attached directly or indirectly to magnetic particles; and
    (3) an erythrocyte aggregation reagent;
  performing a single separation step of magnetically enforced sedimentation by placing the separation mixture in a magnetic field such that the erythrocytes, the granulocytes, and the undesired leukocytes form a pellet, leaving a supernatant phase from which over 90% of the granulocytes in the starting sample have been depleted; and
  harvesting the target leukocytes from the supernatant phase.

25. The depletion method of claim 24, wherein the antigen-recognizing moieties specific for granulocytes include moieties specific for CD66b, CD15, and/or CD16.

26. The depletion method of claim 24, wherein the cocktail of reagents also contains antigen-recognizing moieties specific for platelets attached directly or indirectly to magnetic particles.

27. The depletion method of claim 24, wherein the single separation step produces a supernatant phase from which over 95% of the granulocytes in the sample have been depleted.

28. A depletion method for purifying a target leukocyte subpopulation from a starting sample containing erythrocytes and other types of leukocytes, the method comprising:
  combining the starting sample with a cocktail of reagents to form a separation mixture, wherein the first cocktail comprises as separate components:
    (1) a plurality of different antigen-recognizing moieties specific for cell markers on the other types of leukocytes but not on the target leukocytes, attached directly or indirectly to magnetic particles; and
    (2) an erythrocyte aggregation reagent;
  performing a single separation step of magnetically enforced sedimentation by placing the separation mixture in a magnetic field such that the erythrocytes and the undesired leukocytes form a pellet, leaving a supernatant phase; and
  harvesting the target leukocytes from the supernatant phase;
  wherein the erythrocyte aggregation reagent is selected from hydroxyethyl starch, methylcellulose, and hydroxypropylmethylcellulose (HPMC).

* * * * *